United States Patent [19]

Takaya et al.

[11] Patent Number: 4,621,084
[45] Date of Patent: Nov. 4, 1986

[54] IMIDAZO-HETEROCYCLIC COMPOUNDS AND PHARMACEUTICAL COMPOSITION COMPRISING THE SAME

[75] Inventors: Takao Takaya, Kawanishi; Hisashi Takasugi, Osaka, both of Japan

[73] Assignee: Fujisawa Pharmaceutical Co., Ltd., Osaka, Japan

[21] Appl. No.: 583,609

[22] Filed: Feb. 27, 1984

[30] Foreign Application Priority Data

Feb. 25, 1983 [GB] United Kingdom ............... 8305245

[51] Int. Cl.⁴ .................. A61K 31/41; C07D 471/02; C07D 491/02
[52] U.S. Cl. ........................ 514/225; 546/121; 546/105; 544/353; 544/354; 544/52; 544/51; 544/281; 514/300; 514/249; 514/258
[58] Field of Search .................. 546/121; 544/51, 52, 544/105, 353, 354; 514/300, 225, 228, 249

[56] References Cited

FOREIGN PATENT DOCUMENTS 0052016 7/1982 European Pat. Off. ............ 546/121
0068378 1/1983 European Pat. Off. ............ 546/121
600143 12/1976 U.S.S.R. ............................. 546/121

Primary Examiner—Henry R. Jiles
Assistant Examiner—J. Richter
Attorney, Agent, or Firm—Oblon, Fisher, Spivak, McClelland & Maier

[57] ABSTRACT

New imidazo-heterocyclic compounds of the formula:

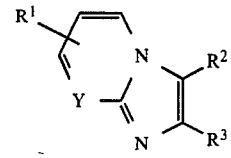

wherein
$R^1$ is hydrogen, lower alkyl or halogen,
$R^2$ is hydrogen, lower alkyl, halogen, aminomethyl optionally substituted with lower alkyl, or piperazin-1-yl-methyl optionally substituted with lower alkyl,
$R^3$ is a partially suturated heterocyclic group selected from benzothiazolinyl, benzoxazolinyl, benzimidazolinyl, 3,4-dihydro-2H-1,4-benzothiazinyl, 3,4-dihydro-2H-1,4-benzoxazinyl and 1,2,3,4-tetrahydroquinoxalinyl, which is substituted with oxo, thioxo, imino or lower alkylimino, and which may be substituted with lower alkyl optionally substituted with lower alkanoyloxy, lower alkoxycarbonyl, pyridyl or lower alkylamino; or an unsaturated heterocyclic group selected from benzoxazolyl and benzimidazolyl, which may be substituted with lower alkyl or pyridyl(lower)alkylthio, and
Y is =N— or a group of the formula:

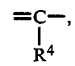

in which $R^4$ is hydrogen, hydroxy, lower alkyl, lower alkoxy or ar(lower)alkoxy, and pharmaceutically acceptable salts thereof, and processes for preparation thereof and pharmaceutical composition comprising the same.

These derivatives and pharmaceutically acceptable salts thereof are useful as cardiotonic agents and antiulcer agents.

11 Claims, No Drawings

IMIDAZO-HETEROCYCLIC COMPOUNDS AND PHARMACEUTICAL COMPOSITION COMPRISING THE SAME

This invention relates to new imidazo-heterocyclic compounds. More particularly, this invention relates to new imidazo-heterocyclic compounds and pharmaceutically acceptable salts thereof which have pharmacological activities, processes for preparation thereof, a pharmaceutical composition comprising the same and method of use thereof.

Accordingly, one object of this invention is to provide the new and useful imidazo-heterocyclic compounds and pharmaceutically acceptable salts thereof.

Another object of this invention is to provide processes for preparation of the imidazo-heterocyclic compounds and pharmaceutically acceptable salts thereof.

A further object of this invention is to provide a pharmaceutical composition comprising said imidazo-heterocyclic compound or a pharmaceutically acceptable salt thereof.

Still further object of this invention is to provide a method of using said imidazo-heterocyclic compound or a pharmaceutically acceptable salt thereof for therapeutic treatment of heart disease and ulcer of human being and animals.

Some imidazopyridine derivatives having a cardiotonic activity have been known as described in Japan Kokai No. 82390/1982 and 102888/1982. However, it has not been known that these compounds possess antiulcer activity.

An intensive study undertaken by the inventors of this invention has resulted in the development of novel imidazo-heterocyclic compounds having a superior cardiotonic activity and antiulcer activity.

The object imidazo-heterocyclic compounds of this invention are novel and represented by the following general formula [I]:

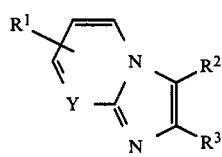

wherein
$R^1$ is hydrogen, lower alkyl or halogen,
$R^2$ is hydrogen, lower alkyl, halogen, aminomethyl optionally substituted with lower alkyl, or piperazin-1-ylmethyl optionally substituted with lower alkyl,
$R^3$ is a partially saturated heterocyclic group selected from benzothiazolinyl, benzoxazolinyl, benzimidazolinyl, 3,4-dihydro-2H-1,4-benzothiazinyl, 3,4-dihydro-2H-1,4-benzoxazinyl and 1,2,3,4-tetrahydroquinoxalinyl, which is substituted with oxo, thioxo, imino or lower alkylimino, and which may be substituted with lower alkyl optionally substituted with lower alkanoyloxy, lower alkoxycarbonyl, pyridyl or lower alkylamino; or an unsaturated heterocyclic group selected from benzoxazolyl and benzimidazolyl, which may be substituted with lower alkyl or pyridyl(lower)alkylthio; and
Y is =N— or a group of the formula:

in which $R^4$ is hydrogen, hydroxy, lower alkyl, lower alkoxy or ar(lower)alkoxy.

Regarding the partially saturated heterocyclic group for $R^3$ in the object compound [I], it is to be understood that said heterocyclic group can be alternatively represented by its tautomers. For example, with regard to oxo-substituted heterocyclic group such as "2-oxo-benzothiazolinyl", it can be represented by its tautomer, i.e. "2-hydroxybenzothiazolyl", and both of these tautomers are in the state of tautomeric equilibrium as represented by the following equilibriums.

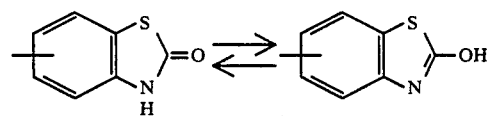

These types of tautomerism have been well known in the art, and it is obvious to a person skilled in the art that both of the tautomeric isomers are equilibrated and lie in the reciprocally convertible state, and accordingly it is to be understood that both of such isomers are included within the same category of the object compound [I].

The heterocyclic group substituted with thioxo, imino or lower alkylimino for $R^3$ also includes their tautomeric isomers, and represented by substantially the same tautomerism as mentioned above.

In the present specification, however, the heterocyclic groups for $R^3$ are represented by using one of the expressions, for instance, "2-oxo-benzothiazolinyl" and the like, only for convenience' sake.

The object compounds [I] and their salts of the present invention can be prepared by the following processes.

Process 1

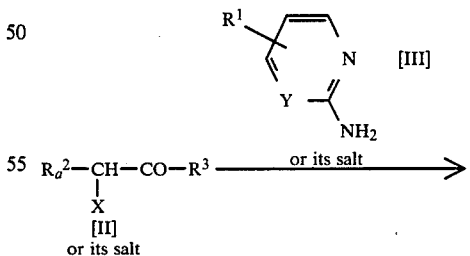

Process 2

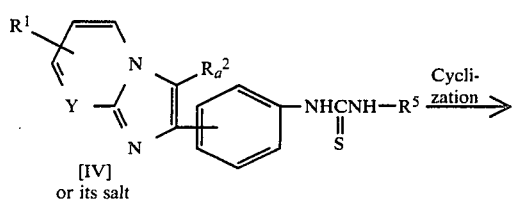

-continued

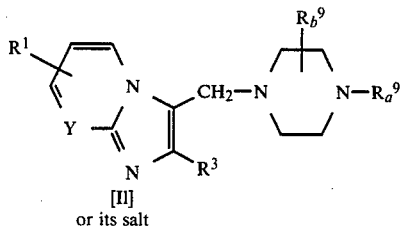

[II]

or its salt wherein
$R^1$, $R^2$, $R^3$ and Y are each as defined above,
$R_a^2$ is hydrogen, lower alkyl or halogen,
$R_a^3$ is a partially saturated heterocyclic group selected from benzothiazolinyl, benzoxazolinyl, benzimidazolinyl, 3,4-dihydro-2H-1,4-benzothiazinyl, 3,4-dihydro-2H-1,4-benzoxazinyl or 1,2,3,4-tetrahydroquinoxalinyl, which is substituted with oxo, thioxo, imino or lower alkylimino, and optionally substituted with lower alkyl,
$R_b^3$ is a partially saturated heterocyclic group selected from benzothiazolinyl, benzoxazolinyl, benzimidazolinyl, 3,4-dihydro-2H-1,4-benzothiazinyl, 3,4-dihydro-2H-1,4-benzoxazinyl and 1,2,3,4-tetrahydroquinoxalinyl, which is substituted with oxo, thioxo, imino or lower alkylimino, and further substituted with lower alkyl optionally substituted with lower alkanoyloxy, lower alkoxycarbonyl, pyridyl or lower alkylamino, and which may be substituted with another lower alkyl,
$R_a^4$ is lower alkoxy or ar(lower)alkoxy,
$R^5$, $R^6$, $R^7$, $R^8_a$, $R_b^8$, $R_a^9$ and $R_b^9$ are each hydrogen or lower alkyl,
A is lower alkylene,
Q is —O— or

and
X is a leaving group.

In the above and subsequent description of the present specification, suitable examples and illustrations for the various definitions to be included within the scope of the invention are explained in detail as follows:

The term "lower" is intended to mean 1 to 6 carbon atom(s) unless otherwise indicated.

Suitable examples of the lower alkyl group for $R^1$, $R^2$, $R_a^2$, $R^4$, $R^5$, $R^6$, $R^7$, $R_a^8$, $R_b^8$, $R_a^9$ and $R_b^9$ may be a straight or branched one such as methyl, ethyl, propyl, isopropyl, butyl, isobutyl, tert-butyl, pentyl, hexyl or the like.

Suitable examples of the lower alkylene group for A may be methylene, ethylene, propylene, trimethylene, tetramethylene, pentamethylene, hexamethylene or the like.

The aminomethyl group and the piperazin-1-ylmethyl group for $R^2$ may be substituted with the above-mentioned lower alkyl. Suitable examples of the aminomethyl group having such substituent(s) may be mono-(lower)alkylaminomethyl [e.g. methylaminomethyl, ethylaminomethyl, propylaminomethyl, etc.], di-(lower)alkylaminomethyl [e.g. dimethylaminomethyl, diethylaminomethyl, dipropylaminomethyl, etc.], or the like. And suitable examples of the piperazin-1-ylmethyl group having such substituent(s) may be 4-methylpiperazin-1-ylmethyl, 4-ethylpiperazin-1-ylmethyl, 2,4-dimethylpiperazin-1-ylmethyl, or the like.

Suitable examples of halogen for $R^1$, $R^2$ and $R_a^2$ may be chlorine, bromine, iodine or fluorine.

The partially saturated heterocyclic group for $R^3$ is benzothiazolinyl, benzoxazolinyl, benzimidazolinyl, 3,4-dihydro-2H-1,4-benzothiazinyl, 3,4-dihydro-2H-1,4-benzoxazinyl or 1,2,3,4-tetrahydroquinoxalinyl, which is substituted with oxo, thioxo, imino or lower alkylimino.

Suitable examples of the partially saturated heterocyclic group substituted with oxo, thioxo, imino or lower alkylimino may be oxo-substituted ones such as 2-oxo-benzothiazolinyl, 2-oxo-benzoxazolinyl, 2-oxobenzimidazolinyl, 3-oxo-3,4-dihydro-2H-1,4-benzothiazinyl, 3-oxo-3,4-dihydro-2H-1,4-benzoxazinyl, 3-oxo-1,2,3,4-tetrahydroquinoxalinyl or the like; thioxo-substituted ones such as 2-thioxo-benzothiazolinyl, 2-thioxo-benzoxazolinyl, 2-thioxo-benzimidazolinyl, 3-thiozo-3,4-dihydro-2H-1,4-benzothiazinyl, 3-thioxo-3,4-dihydro-2H-1,4-benzoxazinyl, 3-thioxo-1,2,3,4-tetrahydroquinoxalinyl or the like; imino-substituted ones such as 2-imino-benzothiazolinyl, 2-imino-benzoxazolinyl, 2-imino-benzimidazolinyl, 3-imino-3,4-dihydro-2H-1,4-benzothiazinyl, 3-imino-3,4-dihydro-2H-1,4-benzoxazinyl, 3-imino-1,2,3,4-tetrahydroquinoxalinyl or the like; lower alkylimino-substituted ones such as 2-(lower)alkylimino-benzothiazolinyl, 2-(lower)alkylimino-benzoxazolinyl, 2-(lower)alkylimino-benzimidazolinyl, 3-(lower)alkylimino-3,4-dihydro-2H-1,4-benzothiazinyl, 3-(lower)alkylimino-3,4-dihydro-2H-1,4-benzoxazinyl, 3-(lower)alkylimino-1,2,3,4-tetrahydroquinoxalinyl or the like.

Suitable examples of the lower alkylimino which is one of the substituents on the above heterocyclic group for $R^3$ may be methylimino, ethylimino, propylimino, isopropylimino, butylimino, isobutylimino, tert-butylimino, pentylimino, hexylimino or the like.

These oxo-, thioxo-, imino- or lower alkyliminosubstituted heterocyclic groups may further be substituted with lower alkyl group(s) as illustrated above. And further, the lower alkyl groups may optionally be substituted with lower alkanoyloxy [e.g. formyloxy, acetoxy, propionyloxy, etc.], lower alkoxycarbonyl [e.g. methoxycarbonyl, ethoxycarbonyl, propoxycarbonyl, butoxycarbonyl, t-butoxycarbonyl, etc.], pyridyl [e.g. 2-pyridyl, 3-pyridyl and 4-pyridyl], or lower alkylamino [e.g. methylamino, ethylamino, propylamino, butylamino, dimethylamino, diethylamino, dibutylamino, etc.].

Accordingly, suitable examples of the partially saturated heterocyclic group having the above-mentioned substituent(s) may be 3-methyl-2-oxo-benzothiazolinyl, 2-imino-benzothiazolinyl, 2-methylimino-benzothiazolinyl, 3-(2-acetoxyethyl)-2-oxo-benzothiazolinyl, 3-(2-dimethylaminoethyl)-2-oxo-benzothiazolinyl, 3-(2-pyridylmethyl)-2-oxo-benzothiazolinyl, 3-methyl-2-oxo-benzoxazolinyl, 3-(t-butoxycarbonylmethyl)-2-oxo-benzoxazolinyl, 4-methyl-3-oxo-3,4-dihydro-2H-1,4-benzothiazinyl, 2-methyl-3-oxo-3,4-dihydro-2H-1,4-benzoxazinyl, 2-ethyl-3-oxo-3,4-dihydro-2H-1,4-benzoxazinyl, or the like.

The unsaturated heterocyclic group for $R^3$ is benzoxazolyl or benzimidazolyl, in which these groups may optionally be substituted with the above-mentioned lower alkyl or pyridyl(lower)alkylthio [e.g. 4-pyridylmethylthio, 3-pyridylmethylthio, 2-pyridylmethylthio, 2-(pyridin-2-yl)ethylthio, 3-(pyridin-2-yl)propylthio, 4-(pyridin-2-yl)butylthio, 6-(pyridin-2-yl)hexylthio, etc.]. Accordingly, suitable examples of the unsaturated heterocyclic group having such substituent(s) may be 2-(pyridin-2-ylmethylthio)benzoxazolyl, 2-methylbenzimidazolyl, 2-(pyridin-2-ylmethylthio)benzimidazolyl or the like.

Suitable examples of the lower alkoxy group for $R^4$ and $R_a^4$ and the lower alkoxy moiety of the ar(lower)alkoxy group for $R^4$ and $R_a^4$ may be methoxy, ethoxy, propoxy, isopropoxy, butoxy, t-butoxy, pentyloxy, hexyloxy or the like.

Suitable examples of the aryl moiety of the ar(lower)alkoxy group for $R^4$ and $R_a^4$ may include phenyl, tolyl, naphthyl and the like.

Accordingly, suitable examples of the ar(lower)alkoxy group for $R^4$ and $R_a^4$ may be benzyloxy, benzhydryloxy, trityloxy, phenethyloxy, 3-phenylpropoxy, naphthylmethoxy or the like.

Suitable examples of the leaving group for X may be halide [e.g. chloride, bromide, iodide, etc.], sulfonate [e.g. benzenesulfonate, tosylate, mesylate, etc.] or the like.

Suitable pharmaceutically acceptable salts of the object compounds [I] are conventional non-toxic salts and include an organic acid salt [e.g. formate, acetate, trifluoroacetate, maleate, tartrate, methanesulfonate, benzenesulfonate, toluenesulfonate, etc.], an inorganic acid salt [e.g. hydrochloride, hydrobromide, sulfate, phosphate, etc.], a salt with an amino acid [e.g. arginine salt, glutamic acid salt, ornithine salt, etc.], a metal salt such as an alkali metal salt [e.g. sodium salt, potassium salt, etc.] and an alkaline earth metal salt [e.g. calcium salt, megnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], and the like.

The processes for preparing the object compounds [I] and salts thereof are explained in detail in the following.

Process 1

The object compound [Ia] and its salt can be prepared by reacting a compound [II] or its salt with a compound [III] or its salt.

Suitable salts of the compounds [II] and [III] may be the same as those exemplified for the compound [I].

Suitable examples of the compound [III] may be 2-aminopyridine, lower alkyl substituted 2-aminopyridine [e.g. 2-amino-3-methylpyridine, 2-amino-3-ethylpyridine, 2-amino-3-hexylpyridine, 2-amino-4-methylpyridine, etc.], lower alkoxy substituted 2-aminopyridine [e.g. 2-amino-3-methoxypyridine, 2-amino-3-ethoxypyridine, 2-amino-3-ethoxy-4-methylpyridine, etc.], ar(lower)alkoxy substituted 2-aminopyridine [e.g. 2-amino-3-benzyloxypyridine, 2-amino-3-phenethyloxypyridine, 2-amino-3-benzyloxy-4-methylpyridine, etc.], halogenated 2-aminopyridine [e.g. 2-amino-5-chloropyridine, 2-amino-5-bromopyridine, 2-amino-3-iodopyridine, 2-amino-4-fluoropyridine, etc.], 2-aminopyrimidine, lower alkyl substituted 2-aminopyrimidine [e.g. 2-amino-4-methylpyrimidine, 2-amino-4-ethylpyrimidine, 2-amino-4-hexylpyrimidine, 2-amino-6-methylpyrimidine, etc.], halogenated 2-aminopyrimidine [e.g. 2-amino-4-chloropyrimidine, 2-amino-4-bromopyrimidine, 2-amino-6-chloropyrimidine, etc.].

This reaction is usually carried out in a conventional solvent such as water, methanol, ethanol, tetrahydrofuran, acetonitrile, 1,2-dimethoxyethane, methylene chloride, chloroform, dimethylacetamide, dimethylformamide, dimethyl sulfoxide or any other organic solvent which does not adversely influence the reaction.

This reaction is preferably conducted in the presence of a base such as alkali metal hydride [e.g. sodium hydride, potassium hydride, etc.], alkaline earth metal hydride [e.g. calcium hydride, magnesium hydride, etc.], alkali metal hydroxide [e.g. sodium hydroxide, potassium hydroxide, etc.], alkali metal carbonate [e.g. sodium carbonate, potassium carbonate, etc.], alkali metal bicarbonate [e.g. sodium bicarbonate, potassium bicarbonate, etc.], alkali metal alkoxide [e.g. sodium methoxide, sodium ethoxide, potassium tert-butoxide, etc.] or the like.

The reaction temperature is not critical, and the reaction is usually carried out at ambient temperature or under warming or heating.

Process 2

The object compound [Ib] and its salt can be prepared by cyclizing a compound [IV] or its salt.

Suitable salts of the compound [IV] may be the same as those exemplified for the compound [I].

Suitable examples of the cyclizing agent to be used in this reaction may be halogen [e.g. bromine, chlorine, iodine, etc.], thionyl halide [e.g. thionyl chloride, thionyl bromide, etc.], sulfuryl halide [e.g. sulfuryl chloride, sulfuryl bromide, etc.] or the like.

This reaction is usually carried out in a conventional solvent which does not adversely influence the reaction such as methylene chloride, dichloroethane, chloroform, carbon tetrachloride, acetic acid, propionic acid or a mixture thereof.

In case that the above-mentioned cyclizing agent is liquid, it can be also used as a solvent.

The reaction temperature is not critical, and the reaction is usually carried out at ambient temperature or under warming or heating.

Process 3

The object compound [Ic] and its salt can be prepared by reacting a compound [V] or its salt with carbon disulfide in the presence of a base (Step 1), and then reacting the reaction product with a compound [VI] or its salt (Step 2).

Suitable salts of the compounds [V] and [VI] may be the same as those exemplified for the compound [I].

Step 1

Suitable examples of the base to be used in this step can be referred to those as illustrated in Process 1.

This reaction is usually carried out in a conventional solvent such as water, methanol, ethanol, propanol, dioxane, tetrahydrofuran, or the like.

The reaction temperature is not critical, and the reaction is usually carried out at ambient temperature or under warming or heating.

The reaction product can be used in the next step with or without isolation. The isolation can be conducted by a conventional manner.

Step 2

The reaction of the product obtained above with the compound [VI] or its salt is usually carried out in a conventional solvent such as water, methanol, ethanol, propanol, dioxane, tetrahydrofuran, dimethylformamide or the like.

This reaction is preferably conducted in the presence of a base as illustrated in Process 1.

The reaction temperature is not critical, and the reaction is usually carried out at ambient temperature or under warming or heating.

Process 4

The object compound [Id] and its salt can be prepared by reacting a compound [Va] or its reactive derivative at the amino group or a salt thereof with a compound [VII] or its reactive derivative at the carboxy group or a salt thereof.

Suitable salts of the compounds [Va] and [VII] may be the same as those exemplified for the compound [I].

Suitable reactive derivatives at the amino group of the compound [Va] include conventional ones used in amidation, for example, Schiff's base type imino or its tautomeric enamine type isomer formed by reaction of the compound [Va] with a carbonyl compound, a silyl derivative formed by reaction of the compound [Va] with a silyl compound such as trimethylsilylacetamide, bis(trimethylsilyl)acetamide or the like, a derivative formed by reaction of the compound [Va] with phosphorus trichloride or phosgene, and the like.

Suitable reactive derivative at the carboxy group of the compound [VII] may include an acid halide, an acid anhydride, an ester, an activated amide, an activated ester and the like.

Suitable examples of such reactive derivatives may be an ester such as lower alkyl ester [e.g. methyl ester, ethyl ester, propyl ester, hexyl ester, etc.], acid chloride, an acid azide, a mixed acid anhydride with an acid such as substituted phosphoric acid [e.g. dialkylphosphoric acid, phenylphosphoric acid, etc.], aliphatic carboxylic acid [e.g. pivalic acid, acetic acid, trichloroacetic acid, etc.] or the like, a symmetrical acid anhydride, an activated amide with imidazole, triazole or dimethylpyrazole, an activated ester with N-hydroxysuccinimide, N-hydroxyphthalimide or 1-hydroxy-6-chlorobenzotriazole, and the like.

The reactive derivatives of the compounds [Va] and [VII] can be selected according to the kinds of the compounds [Va] and [VII], respectively.

When the compound [VII] is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodiimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like.

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvents may be used in a mixture with water.

The reaction may be preferably carried out in the presence of an inorganic or an organic base such as an alkali metal hydroxide [e.g. sodium hydroxide, potassium hydroxide, etc.], an alkali metal carbonate [e.g. sodium carbonate, potassium carbonate, etc.], an alkali metal bicarbonate [e.g. sodium bicarbonate, potassium bicarbonate, etc.], tri(lower)alkylamine [e.g. trimethylamine, triethylamine, etc.], pyridine or its derivative [e.g. picoline, lutidine, 4-dimethylaminopyridine, etc.], or the like. In case that the base or the condensing agent to be used is liquid, it can also be used as a solvent.

The reaction temperature is not critical, and the reaction can be carried out under cooling, at ambient temperature or under warming or heating.

Process 5

The object compound [Ie] and its salt can be prepared by subjecting a compound [VIII] or its salt to reductive-cyclization reaction.

Suitable salts of the compound [VIII] may be the same as those exemplified for the compound [I].

The reduction to be applied in this process may include chemical reduction and catalytic reduction, and can be carried out in a conventional manner.

Suitable reducing agents to be used in chemical reduction are a metal [e.g. tin, zinc, iron, etc.], a combination of such metal and/or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, borane, diborane, etc.], a phosphorus compound [e.g. phosphorus trichloride, phosphorus tribromide, triphenylphosphine, triethylphosphine, etc.] and the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Raney copper, Ullman copper, etc.], or the like.

The chemical reduction and catalytic reduction are usually carried out in a solvent such as water, alcohol [e.g. methanol, ethanol, propanol, etc.] or any other conventional organic solvent such as diethyl ether, dioxane, tetrahydrofuran, etc. or a mixture thereof. Additionally, the aforementioned liquid acids to be used in chemical reduction can also be used as a solvent.

The reaction is usually carried out under cooling to heating.

Process 6

The object compound [Ig] and its salt can be prepared by subjecting a compound [If] or its salt to cleavage reaction of the lower alkoxy or ar(lower)alkoxy group.

The reaction is carried out in the conventional manner, for instance, hydrolysis, reduction or the like.

The hydrolysis is preferably conducted in the presence of an acid.

Preferred examples of the acid may include inorganic acids [e.g. hydrochloric acid, hydrobromic acid, sulfuric acid, etc.], organic acids [e.g. formic acid, acetic acid, trifluoroacetic acid, propionic acid, benzenesulfonic acid, p-toluenesulfonic acid, etc.], and acidic ion-exchange resins.

The hydrolysis is usually carried out in a conventional solvent which does not adversely influence the reaction such as water, methanol, ethanol, dioxane, tetrahydrofuran, dimethyl sulfoxide or a mixture thereof. In case that the aforementioned acid is liquid, it can also be used as a solvent.

The reaction temperature is not critical, and the reaction is usually carried out under warming or heating.

The reduction may be carried out substantially in the same manner as Step 1 of Process 5, and therefore the reaction mode and reaction conditions [e.g. reducing agent, catalyst, solvent, reaction temperature, etc.] of this reaction are to be referred to those as explained in Step 1 of Process 5.

Process 7

The object compound [Ii] and its salt can be prepared by alkylating a compound [Ih] or its salt.

Suitable examples of the alkylating agent to be used in this process may be lower alkyl halide [e.g. methyl iodide, ethyl bromide, propyl bromide, etc.], halogenated lower alkyl ester of lower alkanoic acid [e.g. chloromethyl formate, 2-chloroethyl acetate, 2-bromoethyl acetate, 2-iodoethyl acetate, 6-bromohexyl acetate, 3-bromopropyl propionate, etc.], lower alkyl ester of halo(lower)alkanoic acid [e.g. methyl chloroacetate, methyl bromoacetate, ethyl chloroacetate, propyl bromoacetate, t-butyl chloroacetate, etc.], pyridyl(lower)alkyl halide [e.g. pyridin-2-ylmethyl chloride, pyridin-3-ylmethyl chloride, pyridin-4-ylmethyl chloride, 2-(pyridin-2-yl)ethyl chloride, 2-(pyridin-2-yl)ethyl bromide, 3-(pyridin-2-yl)propyl bromide, etc.], mono(or di)-(lower)alkylamino(lower)alkyl halide [e.g. 2-(methylaminoethyl) chloride, 2-(dimethylamino)ethyl chloride, 3-(dimethylamino)propyl chloride, etc.] or the like.

This reaction is usually carried out in a conventional solvent which does not adversely influence the reaction such as water, methanol, ethanol, dioxane, tetrahydrofuran, benzene, chloroform, methylene chloride, dimethylformamide, dimethyl sulfoxide or a mixture thereof.

This reaction may be preferably conducted in the presence of a conventional base as illustrated in Process 1.

The reaction temperature is not critical, and the reaction is usually carried out at ambient temperature or under warming or heating.

Process 8

The object compound [Ik] and its salt can be prepared by subjecting a compound [Ij] or its salt to Mannich reaction.

Said reaction can be carried out by reacting a compound [Ij] or its salt with formaldehyde or its derivative or a solution thereof and ammonia or lower alkylamine or a salt thereof.

Suitable examples of the formaldehyde derivative may be paraformaldehyde, trioxane or the like. Suitable examples of the solution of formaldehyde or its derivative may be formalin or the like.

The lower alkylamine to be used in this process may include mono(lower)alkylamine [e.g. methylamine, ethylamine, propylamine, hexylamine, etc.] and di(lower)alkylamine [e.g. dimethylamine, diethylamine, dipropylamine, dihexylamine, N-ethyl-N-methylamine, etc.].

This reaction is usually carried out in a conventional solvent which does not adversely influence the reaction such as water, methanol, ethanol, propanol, dioxane, tetrahydrofuran, dimethylformamide, dimethyl sulfoxide or a mixture thereof.

This reaction may be preferably conducted in the presence of a conventional acid such as an inorganic acid [e.g. hydrochloric acid, hydrobromic acid, sulfuric acid, phosphoric acid, etc.], an organic acid [e.g. formic acid, acetic acid, trifluoroacetic acid, benzenesulfonic acid, toluenesulfonic acid, etc.] or the like. In case that the acid is liquid, it can be also used as a solvent.

The reaction temperature is not critical, and the reaction is usually carried out at ambient temperature or under warming or heating.

Process 9

The object compound [Il] and its salt can be prepared by alkylating the nitrogen atom in the group

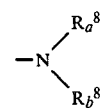

of a of a compound [Ik] or its salt (Step 1), and then reacting the reaction product with a compound [IX] or its salt (Step 2).

Suitable salts of the compound [IX] may be the same as those exemplified for the compound [I].

Step 1

Suitable examples of the alkylating agent to be used in Step 1 may be lower alkyl halide [e.g. methyl iodide, methyl bromide, ethyl iodide, ethyl bromide, etc.], di(lower)alkyl sulfate [e.g. dimethyl sulfate, diethyl sulfate, etc.] or the like.

This reaction is usually carried out in a conventional solvent which does not adversely influence the reaction such as water, methanol, ethanol, propanol, dioxane, tetrahydrofuran, dimethylformamide, dimethyl sulfoxide, benzene, chloroform, methylene chloride or a mixture thereof.

The reaction temperature is not critical, and the reaction is usually carried out at ambient temperature or under warming or heating.

The reaction product can be used in the next step with or without isolation. The isolation can be carried out by a conventional manner.

Step 2

The reaction of the product obtained above with the compound [IX] or its salt is usually carried out in a conventional solvent which does not adversely influence the reaction such as water, methanol, ethanol, propanol, dioxane, dimethylformamide, dimethyl sulfoxide or a mixture thereof.

The reaction temperature is not critical, and the reaction is usually carried out at ambient temperature or under warming or heating.

The starting compounds [II], [IV], [V], [Va] and [VIII] are novel, and can be prepared by the following processes.

Process A

-continued

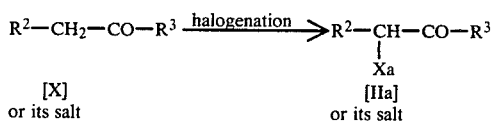

[X] or its salt → [IIa] or its salt

Process B

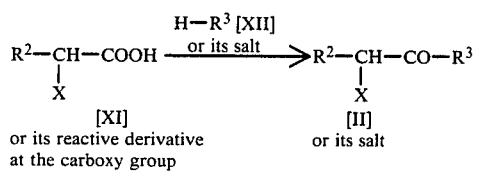

[XI] or its reactive derivative at the carboxy group → [II] or its salt

Process C

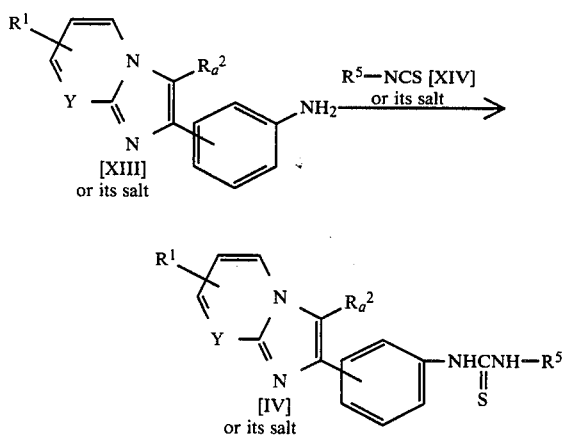

[XIII] or its salt → [IV] or its salt

Process D

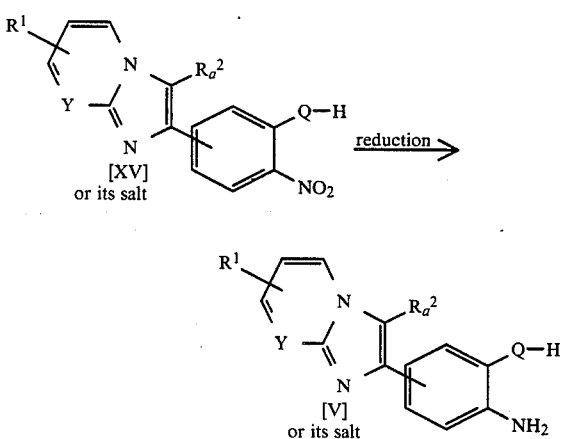

[XV] or its salt → [V] or its salt

Process E

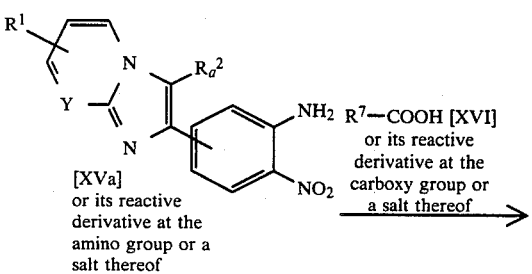

[XVa] or its reactive derivative at the amino group or a salt thereof $R^7$—COOH [XVI] or its reactive derivative at the carboxy group or a salt thereof →

-continued

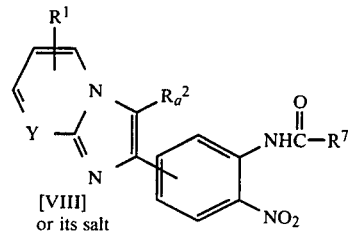

[VIII] or its salt

In the above formulas, $R^1$, $R^2$, $R_a^2$, $R^3$, $R^5$, $R^7$, Y, Q and X are each as defined above, and Xa is halogen.

The processes for preparing the starting compounds [II], [IV], [V] and [VIII] and salts thereof are explained in detail in the following.

Process A

The compound [IIa] and its salt can be prepared by halogenating a compound [X] or its salt.

Suitable salts of the compound [X] may be the same as those exemplified for the compound [I]

Suitable halogenating agent of this reaction may include conventional ones as used in halogenation of aliphatic hydrocarbon containing carbonyl group, for example, halogen [e.g. chlorine, bromine, iodine, etc.], sulfuryl halide [e.g. sulfuryl chloride, sulfuryl bromide, etc.], N-halosuccinim;ide [e.g. N-chlorosuccinimide, N-bromosuccinimide, etc.], pyridinium hydrohalide perhalide [e.g. pyridinium hydrobromide perbromide, pyridinium hydrochloride perchloride, etc.], quarternary ammonium perhalide [e.g. phenyltrimethylammonium perbromide, etc.], ω-trihaloacetophenone [e.g. ω-tribromoacetophenone, etc.], cupric or potassium bromide, selenium oxychloride or the like. These halogenating agents may be selected according to the kind of the starting compound [X] to be used.

This reaction is usually carried out in a conventional solvent such as chloroform, methylene chloride, carbon tetrachloride, dimethylformamide, acetic acid, a mixture or hydrogen halide [e.g. hydrogen bromide, hydrogen chloride, etc.] and acetic acid or the like.

The reaction temperature is not critical, and the reaction is usually carried out at ambient temperature or under warming or heating.

Process B

The compound [II] and its salt can be prepared by reacting a compound [XI] or its reactive derivative at the carboxy group with a compound [XII] or its salt.

Suitable reactive derivative at the carboxy group of the compound [XI] may include an acid halide, an acid anhydride, an activated ester and the like. The suitable examples of the reactive derivatives may be an acid halide [e.g. acid chloride, acid bromide, etc.]; a symmetrical acid anhydride; a mixed acid anhydride with an acid such as aliphatic carboxylic acid [e.g. pivalic acid, isopentanoic acid, etc.], substituted phosphoric acid [e.g. dialkylphosphoric acid, diphenylphosphoric acid, etc.] or the like; an activated ester [e.g. cyanomethyl ester, etc.] or the like. These reactive derivatives can be optionally selected according to the kind of the compound [XI] to be used.

Suitable salts of the compound [XII] may be the same as those exemplified for the compound [I].

This reaction is commonly called "Friedel-Crafts acylation", and usually conducted in the presence of a catalyst.

Suitable catalyst of this reaction may be conventional ones as used in Friedel-Crafts acylation, for example, Lewis acids such as aluminum halide [e.g. aluminum chloride, aluminum bromide, etc.], boron trihalide [e.g. boron trichloride, boron trifluoride, etc.], zinc halide [e.g. zinc chloride, etc.], stannic halide [e.g. stannic chloride, etc.], titanium halide [e.g. titanium tetrachloride, etc.] or the like, protonic acids such as hydrogen halide [e.g. hydrogen fluoride, etc.], sulfuric acid, polyphosphoric acid or the like.

In case that the compound [XI] is used in a free acid form, the reaction is preferably carried out in the presence of the aforementioned protonic acid, and in case that the compound [XI] is used in a reactive derivative form, the reaction is preferably carried out in the presence of the aforementioned Lewis acid.

This reaction is usually carried out in a conventional solvent such as carbon disulfide, methylene chloride, chloroform, carbon tetrachloride, 1,2-dichloroethane, nitromethane, nitrobenzene or any other organic solvent which does not adversely influence the reaction.

The reaction temperature is not critical, and the reaction is usually carried out at ambient temperature or under warming or heating.

Process C

The compound [IV] and its salt can be prepared by reacting a compound [XIII] or its salt with a compound [XIV] or its salt.

Suitable salts of the compound [XIII] may be the same as those exemplified for the compound [I].

Suitable examples of the compound [XIV] may be lower alkyl isothiocyanate [e.g. methyl isothiocyanate, ethyl isothiocyanate, propyl isothiocyanate, hexyl isothiocyanate, etc.] or the like. And suitable salts of the compound [XIV] may be an alkali metal salt [e.g. sodium thiocyanate, potassium thiocyanate, etc.] or the like.

This reaction is usually carried out in a conventional solvent which does not adversely influence the reaction such as water, methanol, ethanol, dioxane, tetrahydrofuran, dimethyl sulfoxide, dimethylformamide or a mixture thereof.

The reaction temperature is not critical, and the reaction is usually carried out at ambient temperature or under warming or heating.

Process D

The compound [V] and its salt can be prepared by reducing a compound [XV] or its salt.

Suitable salts of the compound [XV] may be the same as those exemplified for the compound [I].

This reaction may be carried out substantially in the same manner as Process 5, and therefore the reaction mode and the reaction conditions [e.g. reducing agent, catalyst, solvent, reaction temperature, etc.] of this reaction are to be referred to those as explained in Process 5.

Process E

The compound [VIII] and its salt can be prepared by reacting a compound [XVa] or its reactive derivative at the amino group or a salt thereof with a compound [XVI] or its reactive derivative at the carboxy group or a salt thereof.

Suitable salts of the compound [XVa] may be the same as those exemplified for the compound [I].

This reaction may be carried out substantially in the same manner as Process 4, and therefore the reaction mode and the reaction conditions [e.g. reactive derivative, solvent, base, reaction temperature, etc.] of this reaction are to be referred to those as explained in Process 4.

It is to be noted that each of the object compound [I] and the starting compound [II] include one or more stereoisomers due to asymmetric carbon atoms in the molecule, and all of such isomers of the compound [I] and [II] are included within the scope of this invention.

The new imidazo-heterocyclic compounds [I] and pharmaceutically acceptable salts thereof possess a cardiotonic activity and antiulcer activity, and are useful for a therapeutic treatment of heart disease [e.g. cardiac insufficiency, etc.] and ulcer.

For the purpose of showing pharmaceutical activity of the imidazo-heterocyclic compounds [I], pharmacological test data are illustrated in the following.

[A] CARDIOTONIC ACTIVITY (1) Effect on Spontaneous Contraction of Isolated Guinea Pig Atria Test method :

An atrial strip was removed from male Hartley strain guinea pigs weighing 500–560 g, and suspended in an organ bath containing Tyrode's solution. The bath fluid was maintained at 30° C. and aerated with a gas mixture of 95% $O_2$ and 5% $CO_2$. The atrium was connected to a strain gauge under an initial tension of 0.4–0.6 g and spontaneous atrial contraction was recorded isometrically.

Test compound was dissolved in distilled water and added to the organ bath, and contractile force and heart rate after dosing were compared with those during the predosing period. Experiments were conducted with 3 separate preparations for each concentration.

Test results were represented in terms of percentage of contractile force changes (C.F.C.) calculated by following formula.

$$C.F.C.\ (\%) = \left( \frac{\text{contractile force after dosing}}{\text{contractile force before dosing}} - 1 \right) \times 100$$

Test results:

| Test Compound (Example No.) | Concentration (g/ml) | C.F.C. (%) |
| --- | --- | --- |
| Example 1 | $10^{-5}$ | 35.4 |
| Example 4 | $10^{-5}$ | 25.0 |
|  | $10^{-4}$ | 78.6 |
| Example 5 | $10^{-6}$ | 11.2 |
|  | $10^{-5}$ | 47.5 |
| Example 12 | $10^{-6}$ | 5.7 |
|  | $10^{-5}$ | 30.3 |
| Amrinone* | $10^{-6}$ | 5.1 |
|  | $10^{-5}$ | 15.5 |
|  | $10^{-4}$ | 20.6 |

*3-Amino-5-(4-pyridyl)-2(1H)—pyridinone; known compound actually used as cardiotonic medicine.

(2) Effect on Blood Pressure and heart rate in anesthetized dogs

Test method:

Mongrel dogs of either sex were anesthetized with sodium pentobarbital, 35 mg/kg, i.p. The animals were allowed to breathe spontaneously. The left carotid artery was isolated and a catheter (USCI, #8F) filled with heparinized saline was inserted and advanced into the left ventricle. The catheter was connected to a pressure transducer (Nihonkohden, MPU-0.5A) to measure the left ventricular pressure from which dp/dt max was derived by analog computing. To measure the systemic blood pressure the left femoral artery was cannulated. The blood pressure pulse was used to trigger a heart rate meter. Another catheter was positioned in the vena cave through right femoral vein for injection of drugs. Systemic blood pressure, left ventricular pressure, dp/dt max and heart rate were recorded simultaneously on a polygram (Nihonkohden, RJG-4008).

Test compound was dissolved in distilled water (0.2 ml/kg) or dimethyl sulfoxide (0.04 ml/kg) and injected into the femoral vein. The parameters after dosing were compared with those during the predosing period.

Test results were represented in terms of percentage of dp/dt max changes (dp/dt M.C) calculated by following formula.

$$dp/dt\ M.C\ (\%) = \left(\frac{dp/dt\ \text{max after dosing}}{dp/dt\ \text{max before dosing}} - 1\right) \times 100$$

Test results:

| Test Compound (Example No.) | Dose (mg/kg) | dp/dt M.C (%) |
| --- | --- | --- |
| Example 5 | 1.0 | 83.1 |
| Amrinone | 0.1 | 9.0 |
|  | 1.0 | 80.0 |

[B] ANTIULCER ACTIVITY (1) Inhibition on stress ulcer

Test method:

Five male Sprague-Dawley rats, aged 7 weeks and weighing about 200 g were used per group for the study on stress ulcer after the fast for 24 hours. Each animal was immobilized in a restrain cage and immersed to a level of the xiphoid in a water bath kept 22° C. The test compound suspended in 0.1% methylcellulose solution was administered orally (5 ml/kg) just before the immobilization. Seven hours later, the animals were sacrificed and their stomachs were removed. The stomach was then fixed with 2% formalin. The area of ulcers was measured for each animal. The mean area (mm2) in the test animals was compared with that in the control animals. Test results:

| Test Compound (Example No.) | Dose (mg/kg) | Inhibition (%) |
| --- | --- | --- |
| Example 4 | 32 | 80.5 |
| Example 10 | 32 | 88.1 |
| Example 11 | 32 | 92.5 |
| Example 16 | 32 | 98.0 |
|  | 10 | 35.4 |
| Example 36 | 32 | 87.2 |

(2) Inhibition ethanol ulcer

Test method:

Five male Sprague-Dawley rats, aged 7 weeks and weighing about 200 g, were used per group for the study on ethanol ulcer after the fast for 24 hours.

Test compound was suspended in 0.1% methylcellulose aqueous solution, and the suspension (5 ml/kg) was orally given to each rat.

The control group was given a vehicle, i.e. 0.1% methylcellulose aqueous solution (5 ml/kg), alone in the same way.

Absolute ethanol (5 ml/kg) was orally administered 30 minutes after dosing with test compound, and one hour later, the rats were sacrificed and their stomachs were removed. The area of ulcers of each rat was measured. The mean area (mm$^2$) in the medicated group was compared with that in the control group. Test results:

| Test Compound (Example No.) | Dose (mg/kg) | Inhibition (%) |
| --- | --- | --- |
| Example 16 | 10 | 50.0 |
| Example 11 | 10 | 80.7 |

As being apparent from the above test results, the object compounds [I] of the present invention are useful as cardiotonic medicines and antiulcer medicines.

For therapeutic administration, the object compound [I] of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as capsule, tablet, dragee or suppository, or in a liquid form such as solution, suspension or emulsion. If needed, there may be included in the above preparation auxiliary substance, stabilizing agent, wetting or emulsifying agent, buffer or any other commonly used additives.

The effective ingredient may usually be administered with a unit dose of 0.05 mg/kg to 500 mg/kg, 1 to 4 times a day. However, the above dosage may be increased or decreased according to age, weight, conditions of the patient or the administering method.

The following preparations and examples are given only for the purpose of illustrating the present invention in more detail.

Preparation 1

Bromine (2.4 g) was added to the solution of 5-acetyl-2-benzothiazolinone (2.9 g) in a mixture of methylene chloride (60 ml) and acetic acid (10 ml) at 32° C. to 35° C. with stirring and the mixture was stirred at the same temperature for an hour. The resulting precipitate was collected by filtration, washed with methylene chloride and dried over phosphorus pentoxide to give 5-bromoacetyl-2-benzothiazolinone (2.4 g). mp 249° C. (dec.)

The filtrate was concentrated to afford precipitate, which was collected by filtration and washed with diisopropyl ether to give the second crop of the desired compound (1.2 g).

IR (Nujol): 3200, 1710, 1675, 1590 cm$^{-1}$.

NMR (DMSO-d$_6$, δ): 4.87 (2H, s), 7.23 (1H, d, J=8 HZ), 7.93 (1H, dd, J=2,8 Hz), 8.27 (1H, d, J=2 Hz), 12.30 (1H, br.s).

Preparation 2

5-Bromoacetyl-3-methyl-2-benzothiazolinone (16.3 g) was prepared in the substantially same manner as that of Preparation 1 from 5-acetyl-3-methyl-2-benzothiazolinone (11.5 g) and bromine (9.6 g). mp 119°–120° C. (dec.).

IR (Nujol): 1670, 1590, 1500 cm$^{-1}$.

Preparation 3

To a suspension of aluminum chloride (91.8 g) in carbon disulfide (200 ml) was added 2-bromopropionyl bromide (50 g) and 2-benzothiazolinone (20 g) and the resulting solution was refluxed for 6 hours with stirring. The reaction mixture was poured into ice-water and extracted with ethyl acetate. The extract was washed with brine and dried over magnesium sulfate. The solvent was removed in vacuo to give a residue, which was washed with diisopropyl ether and recrystallized from a mixture of ethyl acetate and diethyl ether to give 5-(2-bromopropionyl)-2-benzothiazolinone (32.3 g).

mp. 135° C. (dec.),

IR (Nujol): 1715, 1685, 1670, 1590 cm$^{-1}$.

NMR (DMSO-d$_6$, δ): 1.80 (3H,d,J=6 Hz), 5.76 (1H,q,J=6 Hz), 7.27 (1H,d,J=8 Hz), 8.00 (1H,dd,J=2,8 Hz), 8.28 (1H,d,J=2 Hz), 12.02 (1H,s).

Preparation 4

A mixture of aluminum chloride (51.2 g) and 2-bromopropionyl bromide (25 g) in carbon disulfide (100 ml) was stirred at 35° C. to 40° C. for 30 minutes. To the mixture was added 3-methyl-2-benzothiazolinone (12.7 g) and the resulting mixture was stirred at 40° C. to 45° C. for 5 hours. The reaction mixture was poured into ice-water and extracted with ethyl acetate. The extract was washed with brine, dried over magnesium sulfate and evaporated in vacuo to afford a crystalline residue. The residue was washed with diisopropyl ether to give 5-(2-bromopropionyl)-3-methyl-2-benzothiazolinone (17.0 g).

mp. 115°–116° C.,

IR (Nujol): 1650, 1590, 1500 cm$^{-1}$.

NMR (DMSO-d$_6$, δ): 1.48 (3H,d,J=6 Hz), 3.45 (3H,s), 5.82 (1H,q,J=6 Hz), 7.40 (1H,d,J=9 Hz), 8.07 (1H,dd,J=2,9 Hz), 8.35 (1H,d,J=2 Hz). Mass. 301 (M+1).

Preparation 5

6-(2-Bromopropionyl)-4-methyl-2H-1,4-benzothiazin-3(4H)-one (19.45 g) was prepared in the substantially same manner as that of Preparation 4 from 4-methyl-2H-1,4-benzothiazin-3(4H)-one (12.6 g) and 2-bromopropionyl bromide (25 g).

IR (Nujol): 1680, 1590, 1565 cm$^{-1}$.

NMR (DMSO-d$_6$, δ): 1.80 (3H, d, J=7 Hz), 3.42 (3H s), 3.60 (2H, s), 5.88 (1H, q, J=7 Hz), 7.55 (1H, d, J=6 Hz), 7.63 (1H, d, J=2 Hz), 7.73 (1H, dd, J=2,6 Hz).

Preparation 6

5-(2-Bromopropionyl)-3-methyl-2-benzoxazolinone (14.7 g) was prepared in the substantially same manner as that of Preparation 4 from 3-methyl-2-benzoxazolinone (11.5 g) and 2-bromopropionyl bromide (25 g).

mp. 138°–140° C. (dec.).

IR (Nujol): 1760, 1670, 1630, 1605 cm$^{-1}$.

NMR (DMSO-d$_6$, δ): 1.78 (2H, d, J=7 Hz), 3.38 (3H, s), 5.83 (1H, q, J=7 Hz), 7.37 (1H, d, J=8 Hz), 7.90 (1H, d, J=2 Hz), 8.00 (1H, dd, J=2,8 Hz).

Preparation 7

To a solution of 6-propionyl-2-methyl-3-oxo-3,4-dihydro-2H-1,4-benzoxazine (3.4 g) and 30% hydrogen bromide-acetic acid (10 ml) in acetic acid (50 ml) was added pyridinium hydrobromide perbromide (5.12 g) at ambient temperature and the mixture was stirred for 2 hours at the same temperature. The reaction mixture was poured into water. The resultant precipitate was collected by filtration and dissolved in a mixture of ethyl acetate and tetrahydrofuran. The organic solution was washed with a saturated aqueous solution of sodium bicarbonate and brine. The solvent was dried over magnesium sulfate and removed in vacuo to afford a crystalline residue, which was washed with diisopropyl ether to give 6-(2-bromopropionyl)-2-methyl-3-oxo-3,4-dihydro-2H-1,4-benzoxazine (3.8 g).

IR (Nujol): 1705, 1675, 1610 cm$^{-1}$.

NMR (DMSO-d$_6$, δ): 1.48 (3H, d, J=7 Hz), 1.78 (3H, d, J=7 Hz), 4.83 (1H, q, J=7 Hz), 5.68 (1H, q, J=7 Hz), 7.10 (1H, d, J=9 Hz), 7.62 (1H, d, J=2 Hz), 7.73 (1H, dd, J=2, 9 Hz), 10.85 (1H, s).

Preparation 8

6-(2-Bromopropionyl)-3-oxo-3,4-dihydro-2H-1,4-benzoxazine (4.3 g) was prepared in substantially the same manner as that of Preparation 7 from 6-propionyl-3-oxo-3,4-dihydro-2H-1,4-benzoxazine (3.7 g).

mp. 204°–206° C.

IR (Nujol): 1715, 1685, 1665, 1610 cm$^{-1}$.

NMR (DMSO-d$_6$, δ): 1.93 (3H, d, J=7 Hz), 4.72 (2H, s), 5.70 (1H, q, J=7 Hz), 7.08 (1H, d, J=8 Hz), 7.28 (1H, d, J=2 Hz), 7.75 (1H, dd, J=2, 8 Hz), 10.83 (1H, s).

Preparation 9

6-(2-Bromopropionyl)-2-ethyl-3-oxo-3,4-dihydro-2H-1,4-benzoxazine (6.8 g) was prepared in substantially the same manner as that of Preparation 7 from 6-propionyl-2-ethyl-3-oxo-3,4-dihydro-2H-1,4-benzoxazine (5.83 g).

mp. 155°–158° C.

IR (Nujol): 3300, 1705, 1685, 1600 cm$^{-1}$.

NMR (DMSO-d$_6$, δ): 1.00 (3H, t, J=7 Hz), 1.80 (2H, m), 1.78 (3H, d, J=7 Hz), 4.72 (1H, t, J=7 Hz), 5.72 (1H, q, J=7 Hz), 7.14 (1H, d, J=8 Hz), 7.60 (1H, d, J=2 Hz), 7.78 (1H, dd, J=2, 8 Hz), 10.85 (1H, s).

Preparation 10

A mixture of aluminum chloride (40 g) and 2-bromopropionyl bromide (32.4 g) in carbon disulfide (100 ml) was refluxed with stirring for 30 minutes. To the resultant mixture was added 2-benzoxazolinone (13.5 g) and the mixture was refluxed under stirring for 7 hours. The reaction mixture was poured into ice-water and extracted with ethyl acetate. The extract was washed with brine and dried over magnesium sulfate. The solvent was evaporated in vacuo to afford a crystalline residue, which was recrystallized from a mixture of ethyl acetate and diethyl ether to give 5-(2-bromopropionyl)-2-benzoxazolinone (13.5 g). mp. 191°–193° C.

IR (Nujol): 3170, 1780, 1662, 1625, 1610 cm$^{-1}$.

NMR (DMSO-d$_6$, δ): 1.82 (3H, d, J=7 Hz), 4.43 (1H, br. s), 5.80 (2H, q, J=7 Hz), 7.20 (1H, d, J=9 Hz), 7.90 (1H, d, J=2 Hz), 7.92 (1H, dd, J=2, 9 Hz).

Preparation 11

A mixture of aluminum chloride (120 g) and 2-bromobutyryl bromide (48 g) in carbon disulfide (120 ml) was stirred for 30 minutes at ambient temperature.

To the resultant mixture was added 3-methyl-2-benzothiazolinone (23 g) and the mixture was stirred for an hour at ambient temperature. The solvent was removed by evaporation at 60°–70° C. and stirred for an hour under the same condition. The reaction mixture was poured into ice-water (360 g) and extracted with chloroform (100 ml×2). The extract was washed with water and dried over magnesium sulfate. The solvent was evaporated in vacuo and the residue was subjected to column chromatography on silica gel (300 g) by eluting with benzene. The fractions containing the desired compound were combined and the solvent was removed by distillation to give 5-(2-bromobutyryl)-3-methyl-2-benzothiazolinone (27.18 g).

IR (Nujol): 1690, 1680, 1670, 1660, 1590 cm$^{-1}$.

NMR (DMSO-d$_6$, δ): 1.02 (3H, t, J=7 Hz), 1.7-2.4 (2H, m), 3.45 (3H, s), 5.65 (1H, t, J=7 Hz), 7.42 (1H, d, J=9 Hz), 8.10 (1H, dd, J=2 Hz, 9 Hz), 8.36 (1H, d, J=2 Hz).

Preparation 12

A solution of 7-methyl-2-(4-aminophenyl)imidazo-[1,2-a]pyridine (14.9 g) and methyl isothiocyanate (6.4 g) in dimethyl sulfoxide (400 ml) was stirred at 50° C. for 10 hours. The reaction mixture was poured into water (1 l) and the resultant precipitate was collected by filtration, washed with water and ethyl acetate successively and dried over phosphorus pentoxide to give 7-methyl-2-[4-(3-methylthioureido)-phenyl]imidazo[1,2-a]pyridine (16.2 g).

IR Nujol): 1640, 1610, 1555, 1515 cm$^{-1}$.

NMR (CF$_3$COOH, δ): 2.37 (3H, s), 3.33 (3H, s). 7.43 (1H, d, J=7 Hz), 7.63 (2H, d, J=9 Hz), 7.78 (1H, s), 8.07 (2H, d, J=9 Hz), 8.27 (1H, s), 8.57 (1H, d, J=7 Hz), 9.60 (1H, m).

Preparation 13

3,7-Dimethyl-2-[4-(3-methylthioureido)phenyl]-imidazo[1,2-a]pyridine (4.32 g) was prepared in substantially the same manner as that of Preparation 12 from 3,7-dimethyl-2-(4-aminophenyl)imidazo[1,2-a]pyridine (4.75 g) and methyl isothiocyanate (6 g).

mp. 219°–220° C.

IR (Nujol): 3360, 1640, 1610, 1590, 1550, 1535, 1500 cm$^{-1}$.

NMR (DMSO-d$_6$, δ): 2.36 (3H, s), 2.62 (3H, s), 2.96 (3H, d, J=4 Hz), 6.78 (1H, dd, J=2 Hz, 7 Hz), 7.34 (1H, s), 7.52 and 7.79 (4H, ABq, J=9 Hz), 8.18 (1H, d, J=7 Hz), 9.58 (1H, s).

Preparation 14

3-Methyl-2-[4-(3-methylthioureido)phenyl]imidazo-[1,2-a]pyridine (2.6 g) was prepared in substantially the same manner as that of Preparation 12 from 3-methyl-2-(4-aminophenyl)imidazo[1,2-a]pyridine (5.4 g) and methyl isothiocyanate (3.4 g). mp. 206°–208° C. (dec.).

IR (Nujol): 3160, 1610, 1580, 1550, 1520 cm$^{-1}$.

NMR (CF$_3$COOH, δ): 2.81 (3H, s), 3.36 (3H, s), 7.70 and 7.92 (4H, ABq, J=7 Hz), 8.03 (3H, s), 8.60 (1H, s)

Preparation 15

6-Chloro-3-methyl-2-[4-(3-methylthioureido)phenyl]-imidazo[1,2-a]pyridine (4.57 g) was prepared in substantially the same manner as that of Preparation 12 from 6-chloro-3-methyl-2-(4-aminophenyl)imidazo[1,2-a]-pyridine (4.4 g) and methyl isothiocyanate (3.74 g).

mp. 169°–170° C.

IR (Nujol): 3370, 3150, 1650, 1625, 1610, 1540, 1510 cm$^{-1}$.

NMR (CF$_3$COOH, δ): 2.76 (3H, s), 3.31 (3H, s), 7.4-7.8 (1H, m), 7.66 and 7.90 (4H, ABq, J=9 Hz), 8.02 (1H, s), 8.50 (1H, dd, J=2 Hz, 7 Hz).

Preparation 16

A solution of 3,7-dimethyl-2-(4-hydroxy-3-nitrophenyl)imidazo[1,2-a]pyridine (2.6 g) in a mixture of ethanol (200 ml) and tetrahydrofuran (100 ml) was hydrogenated over 10% palladium-carbon (wet. 2.0 g) under an atomospheric pressure of hydrogen at ambient temperature for 3 hours. The catalyst was filtered off and the filtrate was evaporated in vacuo. The residue was recrystallized from a mixture of ethyl acetate and tetrahydrofuran to give 3,7-dimethyl-2-(3-amino-4-hydro-xyphenyl)imidazo[1,2-a]pyridine (1.25 g). mp. 251°–253° C.

IR (Nujol): 3370, 1620 cm$^{-1}$.

NMR (DMSO-d$_6$, δ): 2.35 (3H, s), 2.55 (3H, s), 6.72 (1H, dd, J=2, 8 Hz), 6.75 (1H, d, J=8 Hz), 6.88 (1H, d, J=7 Hz), 7.13 (1H, d, J=2 Hz), 7.25 (1H, s), 8.17 (1H, d, J=7 Hz).

Preparation 17

2-(3-Amino-4-hydroxyphenyl)-3-methylimidazo-[1,2-a]pyridine (2.46 g) was prepared in substantially the same manner as that of Preparation 16 from 2-(4-hydroxy-3-nitrophenyl)-3-methylimidazo[1,2-a]pyridine (4.7 g). mp. 251°–254° C. (dec.).

IR (Nujol): 3430, 3350, 1650, 1605, 1500 cm$^{-1}$.

NMR (DMSO-d$_6$, δ): 2.60 (3H, s), 6.87 (2H, s), 6.87-7.77 (4H, m), 8.35 (1H, d, J=7 Hz). Mass. 239 (M$^+$).

Preparation 18

2-(3,4-Diaminophenyl)-3,7-dimethylimidazo[1,2-a]pyridinie (4.7 g) was prepared in substantially the same manner as that of Preparation 17 from 2-(4-amino-3-nitrophenyl)-3,7-dimethylimidazo[1,2-a]pyridine (7.5 g).

NMR (CF$_3$COOH, δ): 2.73 (3H, s), 2.8 (3H, s), 7.38-7.62 (1H, m), 7.67-7.83 (1H, br), 7.92-8.1 (2H, br), 8.1-8.48 (2H, m).

Preparation 19

To 35 ml of nitric acid (fuming, d=1.50) was added portionwise 3,7-dimethyl-2-(4-acetamidophenyl-)imidazo-[1,2-a]pyridine (5.6 g) at 3°–10° C. for a period of 10 minutes and the mixture was stirred for 30 minutes at the same temperature. The reaction mixture was poured into ice-water (500 ml) and the precipitates collected by filtration, were washed with water (100 ml×4) and dried over phosphorus pentoxide under reduced pressure to give 3,7-dimethyl-2-(4-acetamido-3-nitrophenyl)-imidazo[1,2-a]pyridine (3.3 g). mp. 204°–208° C. (dec.).

IR (Nujol): 3350, 1700, 1655, 1625, 1580, 1530, 1510 cm$^{-1}$.

NMR (CF$_3$COOH, δ): 2.54 (3H, s). 2.72 (3H, s), 2.79 (3H, s), 7.52 (1H, d, J=6 Hz), 7.76 (1H, s), 8.10 (1H, d, J=8 Hz), 8.40 (1H, d, J=6 Hz), 8.64 (1H, d, J=2 Hz), 8.90 (1H, d, J=8 Hz).

Mass. 324 (M$^+$).

EXAMPLE 1

A solution of 5-bromoacetyl-2-benzothiazolinone (3.3 g) and 2-aminopyridine (4.2 g) in ethanol was refluxed for 5 hours and the reaction mixture was evaporated in vacuo. To the residue was added a mixture of water and ethyl acetate and the resulting mixture was acidified to pH 1.0 with 10 % hydrochloric acid. The precipitate was collected by filtration and added to a solution of saturated aqueous sodium bicarbonate. The mixture was stirred for 30 minutes. The precipitate was collected by filtration, washed with water and recrystallized from aqueous ethanol to give 5-(imidazo[1,2-a]pyridin-2-yl)-2-benzothiazolinone (0.24 g). mp>270° C.

IR (Nujol): 1680, 1655, 1610, 1530 cm$^{-1}$.
NMR(DMSO-d$_6$, δ): 7.10–8.00 (4H, m), 7.23 (1H, d, J=8 Hz), 8.13 (1H, d, J=2 Hz), 8.57 (1H, s), 8.75 (1H, dd, J=2, 6 Hz), 12.17 (1H, m).
Mass. 267 (M+).

EXAMPLE 2

A solution of 5-bromoacetyl 2-benzothiazolinone (1.75g) and 3-methyl-2-aminopyridine [2.07 g] in acetonitrile [100 ml] was refluxed for 4 hours and the reaction mixture was evaporated in vacuo. To the residue was added a mixture of water, ethyl acetate and tetrahydrofuran. The resulting mixture was adJusted to pH 8.0 with 20% aqueous potassium carbonate. The separated organic layer was washed with brine and dried over magnesium sulfate. The solvent was removed in vacuo to afford a crystalline residue, which was recrystallized from a mixture of tetrahydrofuran and diethyl ether to give 5-(8-methylimidazo-[1,2-a]pyridin-2-yl)-2-benzothiazolinone (1.18 g). mp. 272° C. (dec.).

IR (Nujol): 1680, 1610 cm$^{-1}$.
NMR (DMSO-d$_6$, δ): 2.53 (3H, s), 6.30 (IH.q.J=6 Hz), 7.03 (1H,d,J=6Hz), 7.20 (1H,d,J=8 Hz), 7.90 (1H,dd,J=2,8 Hz), 8.15 (1H,d,J=2 Hz), 8.27 (1H, s), 8.35 (1H,d,J=6 Hz).

EXAMPLE 3

5-(3-Methylimidazo[1,2-? ? pyridin-2-yl)2-benzothiazolinone (1.07 g) was prepared in the substantially same manner as that of Example 2 from 5-(2-bromopropionyl)-2-benzothiazolinone (2.86 g) and 2-aminopyridine (2.8 g). mp.>290° C.(from aqueous ethanol).

IR (Nujol): 2650, 1670, 1610, 1530, 1500 cm$^{-1}$.
NMR (DMSO-d$_6$, δ): 2.67 (3H, s), 7.00–7.83 (3H, m), 7.27 (1H,d,J=8 Hz), 7.75 (1H,dd,J=2.8 Hz), 8.02 (1H,d,J=6 Hz).

EXAMPLE 4

A solution of 5-(2-bromopropionyl)-3-methyl-2-benzothiazolinone (3.0 g) and 2-amino-4-methylpyridine (3.24 g) in acetonitrile (100 ml) was refluxed for 8 hours. The reaction mixture was concentrated to about a half volume and poured into a mixture of water and ethyl acetate. The resulitng mixture was acidified to PHO.5 with 10% hydrochloric acid. The precipitate was collected by filtration and washed successively with water and ethyl acetate. The resulting precipitate was added to a mixture of ethyl acetate, tetrahydrofuran and water, and the mixture was adjust to pH 7.0 with 20% aqueous potassium carbonate solution. The separated organic alyer was washed with brine, dried over magnesium sulfate and evaporated in vacuo to afford a crystalline residue. The residue was recrystallized from a mixture of ethyl acetate and tetrahydrofuran to give 5-(3,7-dimethylimidazo-[1,2-a]pyridin-2-yl)-3-methyl-2-benzothiazolinone (1.96 g).

mp. 204°–206° C.
IR (Nujol): 1680, 1655, 1600, 1575 cm$^{-1}$.
NMR (DMSO-d$_6$, δ): 2.40 (3H, s), 2.63 (3H, s), 3.45 (3H, s), 6.78 (1H,dd,J=2,7 Hz), 7.33 (1H,d,J=2 Hz) 7.40 (1H,d,J=9 Hz), 7.83 (1H,dd,J=2,9 Hz), 8.05 (1H,d,J=2 Hz), 8.20 (1H,d,J=7 Hz).

EXAMPLE 5

5-(3-Methylimidazo[1,2-a]pyridin-2-yl)-3-methyl-2-benzothiazolinone (1.5 g) was prepared in the substantially same manner as that of Example 4 from 5-(2-bromopropionyl)-3-methyl-2-benzothiazolinone (3.0 g) and 2-aminopyridine (2.3 g).

mp. 206°–208° C. (from ethyl acetate),
IR (Nujol): 1680, 1630, 1580 cm$^{-1}$.
NMR (DMSO-d$_6$, δ): 2.67 (3H, s), 3.45 (3H, s), 6.77–7.70 (3H, m), 7.37 (1H,d,J=9 Hz), 7.83 (1H,dd,J=2,9 Hz), 8.07 (1H,d,J=2 Hz), 8.32 (1H,d,J=7 Hz),

EXAMPLE 6

5-(Imidazo[1,2-a]pyridin-2-yl)-3-methyl-2-benzothiazolinone (0.65 g) was prepared in the substantially same manner as that of Example 4 from 5-(2-bromoacetyl)-3-methyl-2-benzothiazolinone (2.3 g) and 2-aminopyridine (2.3 g).

mp. 229°–230° C. (dec.) (from ethyl acetate-tetrahydrofuran).
IR (Nujol): 1680, 1645, 1630, 1605, 1580 cm$^{-1}$.
NMR (DMSO-d$_6$, δ): 3.45 (3H, s), 6.75–7.73 (3H, m), 7.20 (1H,d,J=9 Hz), 8.00 (1H,dd,J=9 Hz), 8.23 (1H,d,J=2 Hz), 8.37 (1H, s), 3.55 (1H,dd,J=2,7 Hz),
Mass. 281 (M+).

EXAMPLE 7

5-(6-Chloro-3-methylimidazo[1,2-a]pyridin-2-yl)-3-mryhyl-2-benzothiazolinone (1.5 g) was prepared in the substantially same manner as that of Example 4 from 5-(2-bromopropionyl)-3-methyl-2-benzothiazolinone (3.0 g) and 2-amino-5-chloropyridine (3.84 g).

mp. 214°–214.5° C. (from ethyl acetate-tetrahydrofuran).
IR (Nujol): 1690, 1660, 1605, 1580 cm$^{-1}$.
NMR (DMSO-d$_6$, δ): 2.63 (3H, s), 3.42 (3H, s), 7.23 (1H,dd,J=2,10 Hz), 7.37 (1H,d,J=8 Hz), 7.60 (1H,d,J=10 Hz), 7.80 (1H,dd,J=28 Hz), 8.05 (1H,d,J=2 Hz), 8.55 (1H,d,J=2 Hz).

EXAMPLE 8

6-(3,7-Dimethylimidazo[1,2-a]pyridin-2-yl)-4-methyl-3-oxo-3,4-dihyro-2H-1,4-benzothiazine (1.9 g) was prepared in the substantially same manner as that of Example 4 from 6-(2-bromopropionyl)-4-methyl-3-oxo-3,4-dihydro-2H-1,4-benzothiazine (3.14 g) and 2-amino-4-methyl-pyridine (3.24 g).

mp. 231° C. (from ethyl acetate).
IR (Nujol): 1660, 1600, 1570 cm$^{-1}$.
NMR (DMSO-d$_6$, δ): 2.38 (3H, s), 2.62 (3H, s), 3.40 (3H, s), 3.53 (2H, s), 6.80 (1H,dd,J=2,7 Hz), 7.35 (1H,d,J=2 Hz), 7.48 (2H, s), 7.62 (1H, s), 8.25 (1H,d,J=7 Hz).
Mass. 323 (M+1).

EXAMPLE 9

6-(3-Methylimidazo[1,2-a]pyridin-2-yl)-4-methyl-3-oxo-3,4-dihydro-2H-1,4-benzothiazine (2.1 g) was prepared in the substantially same manner as that of Example 4 from 6-(2-bromopropionyl)-4-methyl-3-oxo-3,4-dihydro-2H-1,4-benzothiazine (3.14 g) and 2-aminopyridine (2.85 g).

mp. 191° C. (from ethyl acetate-diethyl ether).
IR (Nujol): 1660, 1600, 1565 cm$^{-1}$.
NMR (DMSO-d$_6$, δ): 2.67 (3H,s), 3.43 (3H, s), 3.57 (2H, s), 6.73–7.56 (3H, m), 7.45 (2H, s), 7.62 (1H, s).
Mass. 309 (M+).

EXAMPLE 10

5-(3-Methylimidazo[1,2-]pyridin-2-yl)-3-methyl-2-benzoxazolinone (1.7 g) was prepared in the substantially same manner as that of Example 4 from 5-(2-bromopropionyl)-3-methyl-2-benzoxazolinone (2.84 g) and 2-aminopyridine (2.8 g).

mp. 231°–232° C. (dec.) (from ethyl acetate-tetrahydrofuran).
IR (Nujol): 1760, 1630, 1610 cm$^{-1}$.
NMR (DMSO-d$_6$, δ): 2.67 (3H, s), 3.40 (3H, s), 6.83–7.87 (6H, m), 8.38 (1H,dd,J=2,7 Hz).
Mass. 279 (M+).

EXAMPLE 11

5-(3,7-Dimethylimidazo[1,2-a]pyridin-2-yl)-3-methyl-2-benzoxazolinone (1.35 g) was prepared in the substantially same manner as that of Example 4 from 5-(2-bromopropionyl)-3-methyl-2-benzoxazolinone (2.84 g) and 2-amino-4-methylpyridine (3.24 g).

mp. 240° C. (dec.) (from ethyl acetate-tetrahydrofuran).
IR (Nujol): 1765, 1640, 1610 cm$^{-1}$.
NMR (DMSO-d$_6$, δ): 2.40 (3H, s), 2.63 (3H, s), 3.40 (3H, s), 6.82 (1H,dd,J=2,8 Hz), 7.2–7.4 (2H, m), 7.56–7.8 (2H, m), 8.23 (1H,dd,J=2,6 Hz).
Mass. 293 (M+).

EXAMPLE 12

A solution of 5-(2-bromopropionyl)-2-benzothiazolinone (2.9 g) and 2-aminopyrimidine (2.9 g) in acetonitrile (100 ml) was refluxed for 15 hours with stirring. The reaction mixture was cooled to ambient temperature to give a precipitate, which was collected by filtration. The precipitate was added to a mixture of water and ethyl acetate and the resulting mixture was adjusted to pH 8.0 with 20% aqueous potassium carbonate solution. The precipitate was collected by filtration, washed successively with water and ethanol and dried over phosphorus pentoxide to give 5-(3-methylimidazo-[1,2-a]pyrimidin-2-yl)-2-benzothiazolinone (1.45 g).

mp. >290° C.
IR (Nujol): 2650, 1675, 1610, 1530, 1505 cm$^{-1}$.
NMR (DMSO-d$_6$, δ): 2.67 (3H, s), 7.08 (1H, dd, J=4, 6 Hz), 7.23 (1H, d, J=8 Hz), 7.78 (1H, dd, J=2, 8 Hz), 8.02 (1H, d, J=2 Hz), 8.52 (1H, dd, J=2,4 Hz), 8.80 (1H, dd, J=2, 6 Hz).

EXAMPLE 13

5-(3-Methylimidazo[1,2-a]pyrimidin-2-yl)-3-methyl-2-benzothiazolinone.
mp. 280° C. (dec.) (from tetrahydrofuran-ethyl acetate).
IR (Nujol): 1670, 1610, 1600, 1570, 1520 cm$^{-1}$.
NMR (DMSO-d$_6$, δ): 2.72 (3H, s), 3.40 (3H, s), 7.43 (1H, d, J=9 Hz), 7.63–7.93 (3H, s), 9.00–9.27 (2H, m).

EXAMPLE 14

A mixture of 5-(2-bromobutyryl)-3-methyl-2-benzothiazolinone (3.14 g) and 2-amino-4-picoline (2.7 g) in acetonitrile (30 ml) was stirred for an hour at 65°–70° C. The solvent was distilled off and the residue was dissolved in chloroform (100 ml) and the organic solution was washed with water (50 ml×2). To the separated organic layer was added 1N-hydrochloric acid (50 ml) and stirred for 10 minutes at ambient temperature. The resultant precipitates were collected by filtration and washed twice with 15 ml of cold water and dried over phosphorus pentoxide under reduced pressure to afford 5-(3-ethyl-7-methylimidazo[1,2-a]pyridin-2-yl)-3-methyl-2-benzothiazolinone hydrochloride (1.78 g).

mp. 276°–281° C. (dec.).
IR (Nujol): 3580, 3370, 1675, 1590 cm$^{-1}$.
NMR (CF$_3$COOH, δ): 1.50 (3H, t, J=8 Hz), 2.74 (3H, s), 3.26 (2H, q, J=8 Hz), 3.75 (3H, s), 7.3–8.0 (5H, m), 8.44 (1H, d, J=7 Hz).

EXAMPLE 15

5-(3-Ethylimidazo[1,2-a]pyridin-2-yl)-3-methyl-2-benzothiazolinone (1.47) was prepared in substantially the same manner as that of Example 14 from 5-(2-bromobutyryl)-3-methyl-2-benzothiazolinone (4.71 g) and 2-aminopyridine (3.53 g). mp. 273°–274° C. (dec.).
IR (Nujol): 3480, 3220, 1670, 1595 cm$^{-1}$.
NMR (CF$_3$COOH, δ): 1.53 (3H, t, J=7.5 Hz), 3.32 (2H, q, J=7.5 Hz), 3.75 (3H, s), 7.5–8.1 (5H, m), 8.13 (1H, s), 8.60 (1H, d, J=7 Hz).

EXAMPLE 16

A solution of 6-(2-bromopropionyl)-2-methyl-3-oxo-3,4-dihydro-2H-1,4-benzoxazine (1.5 g) and 2-amino-4-picoline (1.6 g) in acetonitrile (60 ml) was refluxed for 2.5 hours and the reaction mixture was evaporated under reduced pressure. A mixture of ethyl acetate and 5% hydrochloric acid was added to the residue and the resultant mixture was stirred at ambient temperature for 30 minutes. The precipitate was collected by filtration and suspended in water. The mixture was adjusted to pH 7.5 with 20% aqueous potassium carbonate. The resultant mixture was extracted with chloroform and the extract was washed with brine and dried over magnesium sulfate. The solvent was removed in vacuo to afford a crystalline residue, which was recrystallized from a mixture of ethyl acetate and tetrahydrofuran to give 6-(3,7-dimethylimidazo[1,2-a]pyridin-2-yl)-2-methyl-3-oxo-3,4-dihydro-2H-1,4-benzoxazine (0.7 g).

mp. 254°–256° C.
IR (Nujol): 1690, 1605, 1510 cm$^{-1}$.
NMR (DMSO-d$_6$, δ): 1.48 (3H, d, J=7 Hz), 2.37 (3H, s), 2.58 (3H, s), 4.73 (1H, q, J=7 Hz), 6.80 (1H, dd, J=2, 7 Hz), 7.03 (1H, d, J=8 Hz), 7.30 (1H, d, J=2 Hz), 7.43 (1H, dd, J=2, 8 Hz), 7.47 (1H, d, J=2 Hz), 8.18 (1H, d, J=7 Hz), 10.70 (1H, s).

EXAMPLE 17

6-(3,6-Dimethylimidazo[1,2-a]pyridin-2-yl)-2-methyl-3-oxo-3,4-dihydro-2H-1,4-benzoxazine (1.8 g) was prepared in substantially the same manner as that of Example 16 from 6-(2-bromopropionyl)-2-methyl-3-oxo-3,4-dihydro-2H-1,4-benzoxazine (2.4 g) and 2-amino-5-methylpyridine (2.6 g). mp. 232° C. (dec.).
NMR (DMSO-d$_6$, δ): 1.48 (3H, d, J=7 Hz), 2.33 (3H, s), 2.60 (3H, s), 4.72 (1H, q, J=7 Hz), 6.93–7.60 (5H, m), 8.07 (1H, s), 10.72 (1H, s).

EXAMPLE 18

6-(3,8-Dimethylimidazo[1,2-a]pyridin-2-yl)-2-methyl-3-oxo-3,4-dihydro-2H-1,4-benzoxazine (1.55 g) was prepared in substantially the same manner as that of Example 16 from 6-(2-bromoropionyl)-2-methyl-3-oxo-3,4- dihydro-2H-1,4-benzoxazine (2.4 g) and 2-amino-3-methylpyridine (2.6 g). mp. 249°–250° C.

NMR (DMSO-d$_6$, δ): 1.48 (3H, d, J=7 Hz), 2.53 (3H, s), 2.63 (3H, s), 4.72 (1H, q, J=7 Hz), 6.78 (1H, d, J=7 Hz), 6.98 (1H, d, J=6 Hz), 7.05 (1H, d, J=8 Hz), 7.38 (1H, dd, J=2, 8 Hz), 7.52 (1H, d, J=2 Hz), 8.15 (1H, d, J=6 Hz), 10.70 (1H, s).

EXAMPLE 19

6-(3-Methylimidazo[1,2-a]pyridin-2-yl)-2-methyl-3-oxo-3,4-dihydro-2H-1,4-benzoxazine (1.05 g) was prepared in substantially the same manner as that of Example 16 from 6-(2-bromopropionyl)-2-methyl-3-oxo-3,4-dihydro-2H-1,4-benzoxazine (2.2 g) and 2-aminopyridine (2.1 g).
mp. 216°–217° C.

IR (Nujol): 1695, 1620, 1605 cm$^{-1}$.

NMR (DMSO-d$_6$, δ): 1.50 (3H, d, J=7 Hz), 2.65 (3H, s), 4.75 (1H, q, J=7 Hz), 6.83–7.73 (6H, m), 8.32 (1H, dd, J=2,7 Hz), 10.70 (1H, s).

EXAMPLE 20

6-(8-Ethoxy-3-methylimidazo[1,2-a]pyridin-2-yl)-2-methyl-3-oxo-3,4-dihydro-2H-1,4-benzoxazine (1.25 g) was prepared in substantially the same manner as that of Example 16 from 6-(2-bromopropionyl)-2-methyl-3-oxo-3,4-dihydro-2H-1,4-benzoxazine (2.4 g) and 2-amino-3-ethoxypyridine (2.8 g). mp. 180°–181° C. (dec.).

IR (Nujol): 1690, 1632, 1600, 1540 cm$^{-1}$.

NMR (DMSO-d$_6$, δ): 1.43 (3H, t, J=7 Hz), 1.47 (3H, d, J=7 Hz), 2.58 (3H, s), 4.23 (2H, q, J=7 Hz), 4.72 (1H, q, J=7 Hz), 6.63 (1H, dd, J=2, 6 Hz), 6.78 (1H, d, J=6 Hz), 7.03 (1H, d, J=8 Hz), 7.37 (1H, dd, J=2, 8 Hz), 7.52 (1H, d, J=2 Hz), 7.72 (1H, dd, J=2, 6 Hz), 10.70 (1H, s).

EXAMPLE 21

6-(8-Benzyloxy-3-methylimidazo[1,2-a]pyridin-2-yl)-2-methyl-3-oxo-3,4-dihydro-2H-1,4-benzoxazine (2.6 g) was prepared in substantially the same manner as that of Example 16 from 6-(2-bromopropionyl)-2-methyl-3-oxo-3,4-dihydro- 2H-1,4-benzoxazine (2.4 g) and 2-amino-3-benzyloxypyridine (4.8 g). mp. 261°–262° C. (dec.).

IR (Nujol): 1695, 1600, 1550 cm$^{-1}$.

NMR (DMSO-d$_6$, δ): 1.48 (3H, d, J=7 Hz), 2.60 (3H, s), 4.70 (1H, q, J=7 Hz), 5.33 (2H, s), 6.6–6.90 (2H, m), 7.23–7.70 (5H, m), 7.73 (1H, dd, J=2, 5 Hz), 10.67 (1H, s).

EXAMPLE 22

6-(3,7-Dimethylimidazo[1,2-a]pyridin-2-yl)-2-ethyl-3-oxo-3,4-dihydro-2H-1,4-benzoxazine (0.82 g) was prepared in substantially the same manner as that of Example 16 from 6-(2-bromopropionyl)-2-ethyl-3-oxo-3,4-dihydro-2H-1,4-benzoxazine (3.12 g) and 2-amino-4-methylpyridine (3.24 g). mp. 194°–195° C (dec.).

IR (Nujol): 1690, 1605, 1515 cm$^{-1}$.

NMR (DMSO-d$_6$, δ): 1.03 (3H, t, J=7 Hz), 1.83 (2H, m), 2.33 (3H, s), 2.52 (3H, s), 4.48 (1H, t, J=7 Hz), 6.66 (1H, d, J=7 Hz), 6.92 (1H, d, J=8 Hz), 7.20 (1H, s), 7.24 (1H, dd, J=2, 8 Hz), 7.35 (1H, d, J=2 Hz), 8.03 (1H, d, J=7 Hz), 10.40 (1H, s).

EXAMPLE 23

6-(3-Methylimidazo[1,2-a]pyridin-2-yl)-2-ethyl-3-oxo-3,4-dihydro-2H-1,4-benzoxazine (1.07 g) was prepared in substantially the same manner as that of Example 16 from 6-(2-bromopropionyl)-2-ethyl-3-oxo-3,4-dihydro-2H-1,4-benzoxazine (2.28 g) and 2-aminopyridine (2.0 g).
mp. 216°–217° C.

IR (Nujol): 1690, 1630, 1600 cm$^{-1}$.

NMR (DMSO-d$_6$, δ): 1.04 (3H, t, J=7 Hz), 1.85 (2H, m), 2.60 (3H, s), 4.50 (1H, t, J=7 Hz), 6.70–8.56 (6H, m), 8.13 (1H, d, J=7 Hz), 10.40 (1H, s).

EXAMPLE 24

6-(3-Methylimidazo[1,2-a]pyridin-2-yl)-3-oxo-3,4-dihydro-2H-1,4-benzoxazine (0.75 g) was prepared in substantially the same manner as that of Example 16 from 6-(2-bromopropionyl)-3-oxo-3,4-dihydro-2H-1,4-benzoxazine (2.0 g) and 2-aminopyridine (1.8 g). mp. 280°–282° C.

IR (Nujol): 1695, 1665, 1600 cm$^{-1}$.

EXAMPLE 25

6-(3,7-Dimethylimidazo[1,2-a]pyridin-2-yl)-3-oxo-3,4-dihydro-2H-1,4-benzoxazine (1.15 g) was prepared in substantially the same manner as that of Example 16 from 6-(2-bromopropionyl)-3-oxo-3,4-dihydro-2H-1,4-benzoxazine (2.3 g) and 2-amino-4-methylpyridine (2.5 g). mp. 239°–241° C.

IR (Nujol): 1690, 1655, 1640, 1605 cm$^{-1}$.

NMR (DMSO-d$_6$, δ): 2.37 (3H, s), 2.58 (3H, s), 2.62 (2H, s), 6.75 (1H, dd, J=2, 7 Hz), 7.00 (1H, d, J=8 Hz), 7.28 (1H, d, J=2 Hz), 7.48 (1H, d, J=2 Hz), 7.38 (1H, dd, J=2, 8 Hz), 8.13 (1H, d, J=7 Hz).

EXAMPLE 26

6-(3,7-Dimethylimidazo[1,2-a]pyrimidin-2-yl)-2-methyl-3-oxo-3,4-dihydro-2H-1,4-benzoxazine (1.3 g) was prepared in substantially the same manner as that of Example 16 from 6-(2-bromopropionyl)-2-methyl-3-oxo-3,4-dihydro-2H-1,4-benzoxazine (3.0 g) and 2-amino-4-methyl-pyrimidine (3.3 g). mp. 298° C. (dec.).

IR (Nujol): 1690, 1620, 1600, 1525, 1505 cm$^{-1}$.

NMR (DMSO-d$_6$, δ): 1.46 (3H, d, J=7 Hz), 2.48 (3H, s), 2.55 (3H, s), 4.63 (1H, q, J=7 Hz), 6.82 (1H, d, J=7 Hz), 6.91 (1H, d, J=8 Hz), 7.22 (1H, dd, J=2, 8 Hz), 7.32 (1H, d, J=2 Hz), 8.47 (1H, d, J=7 Hz), 10.52 (1H, s).

Mass. 308 (M+).

EXAMPLE 27

6-(3-Methyl-imidazo[1,2-a]pyrimidin-2-yl)-2-methyl-3-oxo-3,4-dihydro-2H-1,4-benzoxazine (1.1 g) was prepared in substantially the same manner as that of Example 16 from 6-(2-bromopropionyl)-2-methyl-3-oxo-3,4-dihydro-2H-1,4-benzoxazine (3.0 g) and 2-aminopyrimidine (2.9 g). mp. 288°–290° C. (dec.).

IR (Nujol): 1705, 1610, 1600, 1535, 1515 cm$^{-1}$.

NMR (DMSO-d$_6$, δ): 1.43 (3H, d, J=7 Hz), 2.58 (3H, s), 4.64 (1H, q, J=7 Hz), 6.92 (1H, d, J=8 Hz), 6.96 (1H, m), 7.24 (1H, dd, J=2, 8 Hz), 7.36 (1H, d, J=2 Hz), 8.34 (1H, dd, J=2, 5 Hz), 8.62 (1H, dd, J=2, 7 Hz), 10.50 (1H, s).

EXAMPLE 28

To a solution of 2-amino-5-propionylbenzothiazole (1.3 g) and 30% hydrogen bromide-acetic acid (3 ml) in acetic acid (15 ml) was added pyridinium hydrobromide perbromide (2.54 g) and the mixture was stirred for 90 minutes. To the reaction mixture was added n-hexane (100 ml). The resultant precipitates were collected by filtration and dissolved in a mixture of water (50 ml) and ethyl acetate (50 ml). The separated organic layer was washed with a saturated aqueous solution of sodium chloride (10 ml) and dried over magnesium sulfate. The solvent was evaporated under reduced pressure and the residue was dissolved in acetonitrile (20 ml). To this mixture was added 2-amino-4-picoline (3.12 g). The mixture was stirred for 6 hours at 50°–60° C. The reaction mixture was evaporated to dryness and the residue was dissolved in a mixture of water (30 ml) and ethyl acetate (30 ml). From the separated organic layer the product was extracted twice with 1N-hydrochloric acid. The aqueous extract was adjusted to pH 7 with 20% aqueous solution of potassium carbonate. The resultant mixture was extracted with chloroform (20 ml×2) and the organic layer was dried over magnesium sulfate. The solvent was distilled off under reduced pressure to give a residue, which was subjected to column chromatography on sillica gel (150 g) eluting with a mixture of chloroform and methanol (20:1). The fractions containing the object compound were combined and the solvent was distilled off to give 2-amino-5-(3,6-dimethylimidazo[1,2-a]pyridin-2-yl)benzothiazole (0.65 g). mp. 245°–247° C. (dec.).

IR (Nujol): 3450, 3320, 3100, 1645, 1540, 1500, 1430, 1325, 1170 cm$^{-1}$.

NMR (CF$_3$COOH, δ): 2.73 (3H, s), 2.80 (3H, s), 7.47 (1H, dd, J=2 Hz, 8 Hz), 7.97 (2H, d, J=2 Hz), 8.35 (1H, dd, J=2 Hz, 8 Hz), 7.6–7.9 (2H, m).

EXAMPLE 29

5-(7-Methylimidazo[1,2-a]pyridin-2-yl)-3-methyl-2-benzothiazolinone (2.0 g) was prepared in substantially the same manner as that of Example 28 from 5-acetyl-3-methyl-2-benzothiazolinone (2.0 g). mp. 264°–265° C. (dec.).

IR (Nujol): 1690, 1670, 1640 cm$^{-1}$.

NMR (CF$_3$COOH, δ): 2.73 (3H, s), 3.73 (3H, s), 7.3–7.6 (1H, m), 7.58 (1H, s), 7.7–8.0 (2H, m), 8.02 (1H, s), 8.16 (1H, s), 8.51 (1H, d, J=7 Hz).

EXAMPLE 30

A solution of 5-(2-bromopropionyl)-2-benzoxazolinone (5.4 g) and 2-amino-4-picoline (6.5 g) in acetonitrile (100 ml) was refluxed for an hour. The reaction mixture was evaporated in vacuo and the residue was poured into a suspension of water and ethyl acetate with stirring. The resultant mixture was acidified to pH 0.8 with 10% hydrochloric acid and stirred for 20 minutes at ambient temperature. The resultant precipitate was collected by filtration. The product was suspended in a mixture of water and ethyl acetate and the resultant mixture was adjusted to pH 8.0 with 20% potassium carbonate. The precipitate was collected by filtration and washed with water and ethyl acetate. The precipitate was recrystallized from an aqueous tetrahydrofuran to afford 5-(3,7-dimethylimidazo[1,2-a]pyridin-2-yl)-2-benzoxazolinone (1.4 g). mp. 276°–280° C. (dec.).

IR (Nujol): 3500, 1762 cm$^{-1}$.

NMR (CF$_3$COOH, δ): 2.70 (3H, s), 2.75 (3H, s), 7.46 (1H, dd, J=2, 7 Hz), 7.62 (1H, s), 7.73 (1H, d, J=2 Hz), 8.37 (1H, d, J=7 Hz), 9.90 (1H, s).

EXAMPLE 31

5-(3-Methylimidazo[1,2-a]pyridin-2-yl)-2-benzoxazolinone (0.9 g) was prepared in substantially the same manner as that of Example 30 from 5-(2-bromopropionyl)-2-benzoxazolinone (2.7 g) and 2-aminopyridine (2.8 g). mp. 296°–298° C. (dec.).

IR (Nujol): 1780 cm$^{-1}$.

NMR (CF$_3$COOH, δ): 7.83 (3H, s), 7.13–8.33 (6H, m), 8.57 (1H, d, J=7 Hz), 9.93 (1H, s).

EXAMPLE 32

5-(8-Benzyloxy-3-methylimidazo[1,2-a]pyridin-2-yl)-2-benzoxazolinone (0.8 g) was prepared in substantially the same manner as that of Example 30 from 5-(2-bromopropionyl)-2-benzoxazolinone (2.1 g) and 2-amino-3-benzyloxypyridine (4.8 g). mp. 264°–265° C. (dec.).

IR (Nujol): 1770, 1550 cm$^{-1}$.

NMR (DMSO-d$_6$, δ): 2.62 (3H, s), 5.33 (2H, s), 6.72–6.88 (2H, m), 7.15 (1H, d, J=9 Hz), 7.28–7.75 (7H, m), 7.92 (1H, dd, J=2, 5 Hz).

EXAMPLE 33

5-(8-Benzyloxy-3-methylimidazo[1,2-a]pyridin-2-yl)-3-methyl-2-benzoxazolinone (2.1 g) was prepared in substantially the same manner as that of Example 30 from 5-(2-bromopropionyl)-3-methyl-2-benzoxazolinone (2.84 g) and 2-amino-3-benzyloxypyridine (4.8 g). mp. 210° C.

IR (Nujol): 1775, 1610, 1550, 1505 cm$^{-1}$.

NMR (CF$_3$COOH, δ): 2.77 (3H, s), 3.58 (3H, s), 5.42 (2H, s), 7.23–7.83 (10H, m), 8.08 (1H, m).

EXAMPLE 34

5-(3,6-Dimethylimidazo[1,2-a]pyridin-2-yl)-3-methyl-2-benzoxazolinone (1.85 g) was prepared in substantially the same manner as that of Example 30 from 5-(2-bromopropionyl)-3-methyl-2-benzoxazolinone (2.3 g) and 2-amino-5-methylpyridine (2.6 g). mp. 247°–249° C.

IR (Nujol): 1760, 1610 cm$^{-1}$.

NMR (CF$_3$COOH, δ): 2.65 (3H, s), 2.78 (3H, s), 3.67 (3H, s), 7.45 (1H, d, J=8 Hz), 7.60–7.93 (3H, m), 7.92 (2H, s), 8.30 (1H, s).

EXAMPLE 35

5-(Imidazo[1,2-a]pyrimidin-2-yl)-3-methyl-2-benzothiazolinone (2.7 g) was prepared in substantially the same manner as that of Example 30 from 5-(2-bromoacetyl)-3-methyl-2-benzothiazolinone (5.72 g) and 2-aminopyrimidine (5.7 g).

IR (Nujol): 1700, 1640, 1605, 1555, 1535 cm$^{-1}$.

NMR (CF$_3$COOH, δ): 3.70 (3H, s), 7.60 (1H, d, J=9 Hz), 7.63–8.00 (2H, m), 8.10 (1H, s), 8.38 (1H, s), 9.22 (2H, m).

EXAMPLE 36

To a solution of 7-methyl-2-[4-(3-methylthioureido)-phenyl]imidazo[1,2-a]pyridine (9.0 g) in chloroform (300 ml) was added portionwise bromine (11.5 g) at ambient temperature and the mixture was refluxed for 6 hours under stirring. The reaction mixture was evaporated in vacuo. To the residue was added 5% hydrochloric acid (300 ml) and the mixture was heated at 80 to 85° C. for 5 hours. The reaction mixture was filtered and the filtrate was adjusted to pH 7.5 with 20% potassium carbonate. From the resultant aqueous solution the product was extracted with a mixture of ethyl acetate and tetrahydrofuran. The organic extract was washed with brine and dried over magnesium sulfate. The solvent was evaporated in vacuo and the residue was subjected to column chromatography on silica gel eluting with a mixture of ethyl acetate and tetrahydrofuran (8:2) and the fraction containing the desired compound was evaporated in vacuo to give 6-(3-bromo-7-methyl imidazo[1,2-a]pyridin-2-yl)-2-methylaminobenzothiazole (1.7 g). mp. 225° C. (dec.).

IR (Nujol): 1630, 1590, 1555 cm$^{-1}$.

NMR (CF$_3$COOH, δ): 2.77 (3H, s), 3.43 (3H, d, J=5 Hz), 7.58 (1H, dd, J=2, 7 Hz), 7.83 (1H, d, J=9 Hz), 7.83 (1H, d, J=2 Hz), 8.11 (1H, dd, J=2, 9 Hz), 8.33 (1H, d, J=2 Hz), 8.60 (1H, d, J=7 Hz), 8.73 (1H, m).

EXAMPLE 37

6-(3,7-Dimethylimidazo[1,2-a]pyridin-2-yl)-2-methylaminobenzothiazole (0.46 g) was prepared in substantially the same manner as that of Example 36 from 3,7-dimethyl-2-[4-(3-methylthioureido)phenyl]-imidazo[1,2-a]pyridine (4.0 g) and bromine (2.08 g).

mp. 191°–194° C.

IR (Nujol): 1615, 1590, 1550 cm$^{-1}$.

NMR (DMSO-d$_6$, δ): 2.37 (3H, s), 2.60 (3H, s), 2.98 (3H, d, J=5 Hz), 6.73 (1H, dd, J=2 Hz, 7 Hz), 7.32 (1H, d, J=2 Hz), 7.45 (1H, d, J=9 Hz), 7.68 (1H, dd, J=2 Hz, 9 Hz), 7.98 (1H, q, J=5 Hz), 8.08 (1H, d, J=2 Hz), 8.15 (1H, d, J=7 Hz).

EXAMPLE 38

6-(3-Methylimidazo[1,2-a]pyridin-2-yl)-2-methylaminobenzothiazole (0.55 g) was prepared in substantially the same manner as that of Example 36 from 3-methyl-2-[4-(3-methylthioureido)phenyl]imidazo[1,2-a]pyridine (2.49 g) and bromine (1.34 g). mp. 251°–254° C. (dec.).

IR (Nujol): 3180, 1630, 1605, 1590, 1530, 1500 cm$^{-1}$.

NMR (CF$_3$COOH, δ): 2.80 (3H, s), 3.40 (3H, d, J=5 Hz), 7.5–8.0 (5H, m), 8.10 (1H, s), 8.50 (1H, d, J=9 Hz), 8.65 (1H, d, J=5 Hz).

EXAMPLE 39

6-(6-Chloro-3-methylimidazo[1,2-a]pyridin-2-yl)-2-methylaminobenzothiazole (1.68 g) was prepared in substantially the same manner as that of Example 36 from 6-chloro-3-methyl-2-[4-(3-methylthioureido)-phenyl]imidazo[1,2-a]pyridine (4.4 g) and bromine (2.05 g).

mp. 273°–274° C. (dec.).

IR (Nujol): 1615, 1586 cm$^{-1}$.

NMR (CF$_3$COOH, δ): 2.80 (3H, s), 3.42 (3H, d, J=5 Hz), 7.92 (4H, d, J=9 Hz), 8.13 (1H, s), 8.60 (1H, s), 8.71 (1H, d, J=5 Hz).

EXAMPLE 40

To a solution of potassium hydroxide (0.67 g) and carbondisulfide (0.91 g) in a mixture of water (1.5 ml) and ethanol (50 ml) was added 7-methyl-2-(3-amino-4-hydroxyphenyl)imidazo[1,2-a]pyridine (2.4 g) and the mixture was refluxed for 5 hours under stirring. To the reaction mixture was added a solution of 2-chloromethylpyridine hydrochloride (4.9 g) and potassium carbonate (3.8 g) in a mixture of water (5 ml) and ethanol (20 ml) at ambient temperature and the resultant mixture was stirred for 3 hours. The precipitate collected by filtration, was suspended in a mixture of water, tetrahydrofuran and ethyl acetate and the mixture was adjusted to pH 11 with 20% potassium carbonate. The separated organic layer was washed with brine and dried over magnesium sulfate. The solvent was removed in vacuo to afford a crystalline residue, which was recrystallized from a mixture of ethyl acetate and tetrahydrofuran to give 5-(7-methylimidazo[1,2-a]pyridin-2-yl)-2-(pyridin-2-ylmethylthio)benzoxazole (1.6 g). mp. 184°–185° C. (dec.).

IR (Nujol): 1640 cm$^{-1}$.

NMR (CF$_3$COOH, δ): 2.72 (3H, s), 5.15 (2H, s), 7.42 (1H, d, J=7 Hz), 7.7–8.8 (9H, m), 8.9 (1H, d, J=6 Hz).

EXAMPLE 41

5-(3-Methylimidazo[1,2-a]pyridin-2-yl)-2-(pyridin-2-ylmethylthio)benzoxazole (1.2 g) was prepared in substantially the same manner as that of Example 40 from 2-(3-amino-4-hydroxyphenyl)-3-methylimidazo[1,2-a]pyridine (2.4 g) and 2-chloromethylpyridine hydrochloride (4.9 g). mp. 116°–118° C.

IR (Nujol): 1590, 1500 cm$^{-1}$.

NMR (DMSO-d$_6$, δ): 2.67 (3H, s), 4.47 (2H, s), 6.8–7.5 (3H, m), 7.50–7.88 (5H, m), 8.00 (1H, s), 8.32 (1H, d, J=6 Hz), 8.58 (1H, dd, J=2, 6 Hz).

EXAMPLE 42

5-(3,7-Dimethylimidazo[1,2-a]pyridin-2-yl)-2-(pyridin-2-ylmethylthio)benzimidazole(1.2g) was prepared in substantially the same manner as that of Example 40 from 2-(3,4-diaminophenyl)-3,7-dimethylimidazo[1,2-a]pyridine (2 g) and 2-chloromethylpyridine hydrochloride (3.89 g).

IR (Nujol): 1655, 1595, 1535 cm$^{-1}$.

NMR (CF$_3$COOH, δ): 2.57 (3H, s), 2.6 (3H, s), 5.23 (2H, s), 7.25–8.91 (10H, m).

EXAMPLE 43

A solution of 3,7-dimethyl-2-(3-amino-4-hydroxyphenyl)imidazo[1,2-a]pyridine (1.27 g) and triethylamine (1.0 g) in tetrahydrofuran (100 ml) was added to 2-bromopropionyl bromide (1.3 g) at ambient temperature. The resultant mixture was stirred at ambient temperature for 2 hours and at 60° to 70° C. for 2 hours. The reaction mixture was evaporated under reduced pressure and the residue was dissolved in a mixture of ethyl acetate and water. The separated organic layer was washed with brine and dried over magnesium sulfate. The solvent was removed in vacuo and the residue was subjected to column chromatography on silica gel eluting with a mixture of chloroform and methanol (9:1). The fractions containing the desired compound were combined and evaporated in vacuo to afford a crystalline residue, which was recrystallized from ethyl acetate to give 6-(3,7-dimethylimidazo[1,2-a]pyridin-2-yl)-2-methyl-3-oxo-3,4-dihydro-2H-1,4-benzoxazine (0.5 g). mp. 254°–256° C.

IR (Nujol): 1690, 1605, 1510 cm$^{-1}$.

NMR (DMSO-d$_6$, δ): 1.48 (3H, d, J=7 Hz), 2.37 (3H, s), 2.58 (3H, s), 4.73 (1H, q, J=7 Hz), 6.80 (1H, dd, J=2, 7 Hz), 7.03 (1H, d, J=8 Hz), 7.30 (1H, d, J=2 Hz), 7.43 (1H, dd, J=2, 8 Hz), 7.47 (1H, d, J=2 Hz), 8.18 (1H, d, J=7 Hz), 10.70 (1H, s).

EXAMPLE 44

A mixture of 3,7-dimethyl-2-(4-acetoamido-3-nitrophenyl)imidazo[1,2-a]pyridine (2 g) in methanol (200 ml) was hydrogenated over 10% palladium on carbon (wet, 400 mg) under an atmospheric pressure of hydrogen at ambient temperature for 2 hours. The catalyst was filtered off and the filtrate was concentrated to 20 ml of volume and allowed to stand overnight. The precipitates were filtered off and the filtrate was concentrated under reduced pressure. The residue was subjected to column chromatography on aluminum oxide (50 g) eluting with chloroform. The fractions containing the object compound were combined and allowed to stand overnight. The resultant yellow needles were collected by filtration and dried under reduced pressure to afford 5-(3,7-dimethylimidazo[1,2-a]pyridin-2-yl)-2-methylbenzimidazole (0.51 g). mp. 250°–253° C. (dec.).

IR (Nujol): 1645, 1630, 1545, 1505 cm$^{-1}$.

NMR ($D_2$+DCl, δ): 2.56 (3H, s), 2.65 (3H, s), 2.96 (3H, s), 7.33 (1H, d, J=6 Hz), 7.5–8.0 (4H, m), 8.36 (1H, d, J=6 Hz).

Mass. 276 (M+).

EXAMPLE 45

A solution of 5-(8-benzyloxy-3-methylimidazo[1,2-a]pyridin-2-yl)-3-methyl-2-benzoxazolinone (1.6 g) in a mixture of ethanol (200 ml) and tetrahydrofuran (100 ml) was hydrogenated over 10% palladium on carbon (wet, 0.5 g) under an atmospheric pressure of hydrogen at ambient temperature for an hour. The catalyst and an insoluble material were filtered off and the filtrate was evaporated in vacuo. The residue was recrystallized from a mixture of tetrahydrofuran and ethanol to give 5-(8-hydroxy-3-methylimidazo[1,2-a]pyridin-2-yl)-3-methyl-2-benzoxazolinone (0.78 g). mp. >280° C.

IR (Nujol): 1770, 1615, 1550 cm$^{-1}$.

NMR ($CF_3COOH$, δ): 2.76 (3H, s), 3.63 (3H, s), 7.33–7.9 (5H, m), 8.10 (1H, t, J=4 Hz).

EXAMPLE 46

A mixture of 5-(3,7-dimethylimidazo[1,2-a]pyridin-2-yl)-2-benzothiazolinone (1.77 g) and sodium hydride (50% suspension in oil, 0.788 g) in dry dimethylformamide (24 ml) was stirred at 40° to 45° C. for 20 minutes. To the resultant mixture was added a solution of 2-diethylaminoethyl chloride hydrochloride (1.55 g) and 1.8 ml of a methanolic solution of sodium methoxide (5 mole/ml) in methanol (30 ml) at ambient temperature. The mixture was stirred for 4 hours under the same condition. The reaction mixture was poured into ice-water (300 ml) and extracted with ethyl acetate. The separated organic layer was re-extracted with 1N hydrochloric acid (25 ml) and the aqueous extract was allowed to stand for 2 hours at ambient temperature to give crystals, which was collected by filtration and dried over phosphorus pentoxide to give 5-(3,7dimethylimidazo[1,2-a]pyridin-2-yl)-3-(2-diethylaminoethyl)-2-benzothiazolinone hydrochloride (0.68 g). mp. 272° C. (dec.).

IR (Nujol): 3370, 2600, 2450, 1675, 1600, 1500 cm$^{-1}$.

NMR ($D_2O$, δ): 1.43 (6H, t, J=7 Hz), 2.52 (3H, s), 2.57 (3H, s), 3.51 (4H, q, J=7 Hz), 3.60 (2H, t, J=6 Hz), 4.42 (2H, t, J=6 Hz), 7.28 (1H, d, J=7 Hz), 7.2–7.7 (4H, m), 8.31 (1H, d, J=7 Hz).

Mass. 394 (M+)

EXAMPLE 47

A mixture of 5-(3-methylimidazo[1,2-a]pyridin-2-yl)-2-benzothiazolinone (2.8 g) and sodium hydride (50% suspension in oil, 0.96 g) in dry dimethylformamide (30 ml) was stirred at ambient temperature for 30 minutes. To the resultant mixture was added 2-bromoethyl acetate (3.34 g) at ambient temperature and stirred for 5 hours under the same condition. The reaction mixture was poured into water and adjusted to pH 7.0 with 10% hydrochloric acid. The neutrallized solution was extracted with ethyl acetate. The extract was washed with brine and dried over magnesium sulfate. The solvent was removed in vacuo and the residue was subjected to column chromatography on silica gel eluting with a mixture of ethyl acetate and diisopropyl ether (8:2). The fractions containing the desired compound was combined and evaporated in vacuo. The crystalline residue was recrystallized from ethyl acetate to afford 5-(3-methylimidazo[1,2-a]pyridin-2-yl)-3-(2-acetoxyethyl)-2-benzothiazolinone (1.3 g). mp. 113°–115° C.

IR (Nujol): 1740, 1670, 1580 cm$^{-1}$.

NMR (DMSO-$d_6$, δ): 1.92 (3H, s), 2.60 (3H, s), 4.27 (4H, s), 6.76–7.97 (5H, m), 8.10 (1H, d, J=2 Hz), 8.25 (1H, dd, J=2, 7 Hz).

Mass. 367 (M+)

EXAMPLE 48

5-(3,7-Dimethylimidazo[1,2-a]pyridin-2-yl)-3-(pyridin-3-ylmethyl)-2-benzothiazolinone (0.92 g) was prepared in substantially the same manner as that of Example 47 from 5-(3,7-dimethylimidazo[1,2-a]pyridin-2-yl)-2-benzothiazolinone (1.48 g) and 3-chloromethylpyridine (1.27 g). mp. 201°–202° C.

IR (Nujol): 3420, 1675, 1585 cm$^{-1}$.

NMR (DMSO-$d_6$, δ): 2.35 (3H, s), 2.60 (3H, s), 5.26 (2H, s), 6.75 (1H, dd, J=2 Hz, 7 Hz), 7.22 (2H, d, J=9 Hz), 7.31 (1H, d, J=2 Hz), 7.79 (1H, dd, J=2.5 Hz, 9 Hz), 8.08 (1H, d, J=2 Hz), 8.18 (1H, d, J=7 Hz), 8.51 (1H, dd, J=2.5 Hz, 9 Hz), 8.65 (1H, d, J=2.5 Hz), 7.79, (1H, dd, J=2 Hz, 9 Hz).

Mass. 386 (M+)

EXAMPLE 49

5-(3,7-Dimethylimidazo[1,2-a]pyridin-2-yl)-3-t-butoxycarbonylmethyl-2-benzoxazolinone (1.5 g) was prepared in substantially the same manner as that of Example 47 from 5-(3,7-dimethylimidazo[1,2-a]pyridin-2yl)-2-benzoxazolinone (2.8 g) and t-butyl chloroacetate (2.25 g). mp. 198°–200° C. (dec.).

IR (Nujol): 1775, 1750, 1640, 1610 cm$^{-1}$.

NMR (DMSO-$d_6$, δ): 1.45 (9H, s), 2.37 (3H, s), 2.60 (3H, s), 4.67 (2H, s), 6.75 (1H, dd, J=2, 7 Hz), 7.23–7.80 (3H, m), 7.73 (1H, s), 8.18 (1H, d, J=7 Hz).

EXAMPLE 50

The mixture of 5-(7-methylimidazo[1,2-a]pyridin-2-yl)-methyl-2-benzothiazolinone (1.9 g), 36% aqueous formaldehyde (1.07 g), 50% aqueous dimethylamine (1.16 g), acetic acid (772 mg) and methanol (10 ml) was stirred for 3 hours at 55°–60° C. The reaction mixture was concentrated under reduced pressure and the residue was dissolved in a mixture of 1N hydrochloric acid (10 ml), water (10 ml) and ethyl acetate (30 ml). The separated aqueous layer was adjusted to pH 7 with 20% aqueous solution of potassium carbonate and the resultant aqueous mixture was extracted with ethyl acetate (50 ml×2). The extract was dried over magnesium sulfate and evaporated under reduced pressure to give a crystalline residue, which was re-crystallized from ethyl acetate to afford pale brown needles of 5-(3-dimethylaminomethyl-7-methylimidazo[1,2-a]pyridin-2-yl)-3-methyl-2-benzothiazolinone (1.56 g). mp. 167°–168° C.

IR (Nujol): 1670, 1570 cm$^{-1}$.

NMR ($CF_3COOH$, δ): 2.72 (3H, s), 3.06 (6H, d, J=4 Hz), 3.73 (3H, s), 5.2 (2H, br s), 7.59 (1H, d, J=8 Hz), 7.64 (1H, s), 7.83 (1H, d, J=8 Hz), 7.91 (1H, d, J=8 Hz), 7.97 (1H, s), 8.85 (1H, d, J=8 Hz).

EXAMPLE 51

5-(3-Dimethylaminomethylimidazo[1,2-a]pyridin-2-yl)-3-methyl-2-benzothiazolinone (6.35 g) was prepared in substantially the same manner as that of Example 50 from 5-(imidazo[1,2-a]pyridin-2-yl)-3-methyl-2benzothiazolinone (8.86 g), 30% aqueous formaldehyde (2.57 g) and 50% aqueous dimethylamine (2.97 g).

mp. 137°–140° C.

IR (Nujol): 1675, 1605 cm$^{-1}$.

NMR (DMSO-d$_6$, δ): 3.45 (6H, s), 3.90 (3H, s), 6.7–8.1 (4H, m), 8.15 (1H, d, J=2 Hz), 8.53 (1H, d, J=7 Hz).

EXAMPLE 52

A mixture of 5-(3-dimethylaminomethylimidazo[1,2-a]-pyridin-2-yl)-3-methyl-2-benzothiazolinone (3.98 g) and methyl iodide (6.0 g) in ethanol (20 ml) was stirred for hours at ambient temperature and for 2 hours at 50°–55° C. The resultant precipitate was collected by filtration, washed with ethanol and dried under reduced pressure to give white powder (5.1 g). A mixture of this powder (2.5 g) and N-methylpiperazine (544.5 mg) in ethanol (24 ml) was refluxed for 2 hours. The resultant precipitates were filtered off and the filtrate was allowed to stand for 3 hours. The crystalline precipitates were collected by filtration, washed with cold ethanol and dried in vacuo to afford 5-[3-(4-methylpiperazin-1-ylmethyl)imidazo[1,2-a]pyridin-2-yl]-3-methyl-2-benzothiazolinone (1.37 g). mp. 191°–193 ° C.

IR (Nujol): 3300, 1660 cm$^{-1}$.

NMR (DMSO-d$_6$, δ): 2.5–2.9 (8H, m), 2.80 (3H, s), 3.46 (3H, s), 4.16 (2H, s), 7.1–7.9 (3H, m), 7.40 (1H, d, J=9 Hz), 7.90 (1H, dd, J=2, 9 Hz), 8.11 (1H, d, J=2 Hz), 8.62 (1H, dd, J=2, 7 Hz).

What we claim is:

1. A compound of the formula:

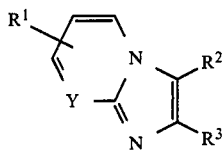

wherein
R$^1$ is hydrogen, lower alkyl or halogen,
R$^2$ is hydrogen, lower alkyl, halogen, aminomethyl, aminomethyl substituted with lower alkyl, piperazin-1-yl-methyl, or piperazin-1-yl-methyl substituted with lower alkyl,
R$^3$ is a partially saturated heterocyclic group selected from the group consisting of benzothiazolinyl, benzoxazolinyl, benzimidazolinyl, 3,4-dihydro-2H-1, 4-benzothiazinyl, 3,4-dihydro-2H-1, 4-benzoxazinyl and 1,2,3,4-tetrahydroquinoxyalinyl, which is substituted by oxo, thioxo, imino or lower alkylimino, and which may be further substituted with lower alkyl or lower alkyl substituted with lower alkanoyloxy, lower alkoxycarbonyl, pyridyl or lower alkylamino; or an unsaturated heterocyclic group selected from the group consisting of benzoxazolyl and benzimidiazolyl, which may be substituted with lower alkyl or pyridyl (lower) alkylthio, and
Y is N or a group of the formula:

in which R$^4$ is hydrogen, hydroxy, lower alkyl, lower alkoxy or ar(lower)alkoxy, and pharmaceutically acceptable salts thereof.

2. The compound of claim 1, wherein
R$^3$ is a partially saturated heterocyclic group selected from the group consisting of benzothiazolinyl, benzoxazolinyl, benzimidazolinyl, 3,4-dihydro-2H-1,4-benzothiazinyl and 3,4-dihydro-2H-1,4-benzoxazinyl, which is substituted with oxo, thioxo, imino or lower alkylimino; and which may be further substituted with lower alkyl or lower alkyl substituted with lower alkanoyloxy, lower alkoxycarbonyl, pyridyl or lower alkylamino; or
an unsaturated heterocyclic group selected from the groups consisting of benzoxazolyl and benzimidazolyl, which may be substituted with lower alkyl or pyridyl(lower) alkylthio.

3. The compound of claim 2, wherein
R$^1$ is hydrogen or lower alkyl,
R$^2$ is lower alkyl or halogen, and
R$^3$ is benzothiazolinyl, benzoxazolinyl or 3,4-dihydro-2H,1,4-benzoxazinyl substituted with oxo or lower alkylamino, or said groups further substituted with lower alkyl 4. The compound of claim 3, whrein
R$^3$ is 3-oxo-3,4-dihyro-2H-1,4-benzoxazinyl, or said group substituted with lower alkyl.

5. The compound of claim 4, which is 6-(3,7-dimethylimidazo[1,2-a]pyridin-2-yl)-2-methyl-3-oxo-3,4-dithydro-2H-1,4-benzoxazine.

6. A compound of claim 3, wherein
R$^3$ is 2-oxo-benzoxazolinyl, or said group substituted with lower alkyl.

7. The compound of claim 6, which is 5-(3,7-dimethylimidazo[1,2-a]pyridin-2-yl)-3-methyl-2-benzoxazolinone.

8. A cardiotonic pharmaceutical composition comprising a cardiotonically effective amount of a compound of claim 1, and a pharmaceutically acceptable, substantially nontoxic carrier or excipient.

9. An antiulcerative pharmaceutical composition comprising an antiulceratively effective amount of a compound of claim 1, and a pharmaceutically acceptable, substantially nontoxic carrier or excipient.

10. A method for cardiotonic treatment which comprises administering to an animal or human in need thereof a cardiotonically effective therapeutic dose of a compound of claim 1.

11. A method for antiulcerative treatment which comprises administering to an animal or human in need thereof an antiulceratively effective therapeutic dose of a compound of claim 1.

* * * * *